(12) United States Patent
Bertani et al.

(10) Patent No.: US 8,217,168 B2
(45) Date of Patent: Jul. 10, 2012

(54) AZABICYCLO [3. 1. 0] HEXYL DERIVATIVES AS MODULATORS OF DOPAMINE $D_3$ RECEPTORS

(75) Inventors: Barbara Bertani, Verona (IT); Susanna Cremonesi, Verona (IT); Stefano Fontana, Verona (IT); Alessandra Pasquarello, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 189 days.

(21) Appl. No.: 12/680,792

(22) PCT Filed: Oct. 1, 2008

(86) PCT No.: PCT/EP2008/063168
§ 371 (c)(1),
(2), (4) Date: Mar. 30, 2010

(87) PCT Pub. No.: WO2009/043884
PCT Pub. Date: Apr. 9, 2009

(65) Prior Publication Data
US 2010/0240661 A1    Sep. 23, 2010

(30) Foreign Application Priority Data
Oct. 2, 2007  (GB) .................................. 0719234.7

(51) Int. Cl.
| C07D 403/06 | (2006.01) |
| C07D 403/14 | (2006.01) |
| C07D 401/14 | (2006.01) |
| C07D 417/14 | (2006.01) |
| C07D 207/36 | (2006.01) |
| C07D 209/02 | (2006.01) |
| A61K 31/53  | (2006.01) |
| A61P 25/18  | (2006.01) |
| A61P 25/30  | (2006.01) |
| A61P 15/12  | (2006.01) |

(52) U.S. Cl. ........................................ 544/182; 514/242
(58) Field of Classification Search .................. 544/182; 514/242
See application file for complete search history.

(56) References Cited

U.S. PATENT DOCUMENTS
4,297,129 A    10/1981  Sanemitsu et al.

FOREIGN PATENT DOCUMENTS
WO    WO 2006/108701 A    10/2006

OTHER PUBLICATIONS

Strange, PG., et al., Trends in Pharmaceutical Sciences, vol. 29, No. 6, 314-321, 2008.*
Joyce et al., Drug Discovery Today, vol. 10, No. 13, 917-925, 2005.*
Freshney et al.,Culture of Animal Cells, A Manual of Basic Technique, Alan R. Liss, Inc., 1983, New York, p. 4.*
Dermer et al., Bio/Technology, 1994, 12:320.*

* cited by examiner

Primary Examiner — Venkataraman Balasubramanian
(74) Attorney, Agent, or Firm — Bonnie L. Deppenbrock

(57) ABSTRACT

The present invention relates to novel compounds of formula (I) or a salt thereof:

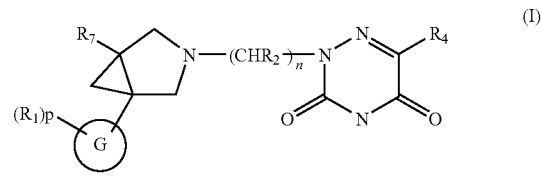

wherein
G is selected from a group consisting of: phenyl, a 5- or 6-membered monocyclic heteroaryl group, or a 8- to 11-membered heteroaryl bicyclic group;
p is an integer ranging from 0 to 5;
$R_1$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 3, 4, 5 or 6;
$R_6$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from: halogen, cyano, $C_{1-4}$alkyl, halo$C_{1-4}$alkyl, $C_{1-4}$alkoxy, $C_{1-4}$alkanoyl;
$R_4$ is selected in the group consisting of: hydrogen, halogen, hydroxy, cyano, $C_{1-4}$alkyl, $C_{3-7}$ cycloalkyl, halo$C_{1-4}$alkyl, $C_{1-4}$alkoxy, halo$C_{1-4}$alkoxy, $C_{1-4}$alkanoyl and NR'R"; or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, halo$C_{1-4}$alkoxy and $SF_5$;
$R_7$ is hydrogen or $C_{1-2}$alkyl;
R' is H, $C_{1-4}$ alkyl or $C_{1-4}$ alkanoyl;
R" is defined as R';
R' and R" taken together with the interconnecting nitrogen atom may form a 5-, 6-membered saturated or unsaturated heterocyclic ring;
and their use in therapy, as modulators of dopamine $D_3$ receptors.

4 Claims, No Drawings

AZABICYCLO [3. 1. 0] HEXYL DERIVATIVES AS MODULATORS OF DOPAMINE $D_3$ RECEPTORS

This application is a 371 of International Application No. PCT/EP2008/063168, filed 1 Oct. 2008, which claims the priority of GB Application No. 0719234.7, filed 2 Oct. 2007, which are incorporated herein in their entirety.

The present invention relates to novel compounds, processes for their preparation, intermediates used in these processes, pharmaceutical compositions containing them and their use in therapy, as modulators of dopamine $D_3$ receptors.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

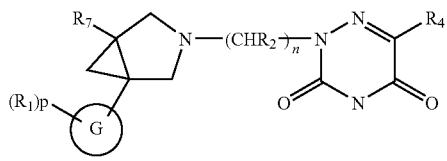

(I)

wherein
G is selected from a group consisting of: phenyl, a 5- or 6-membered monocyclic heteroaryl group, or a 8- to 11-membered heteroaryl bicyclic group;
p is an integer ranging from 0 to 5;
$R_1$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 3, 4, 5 or 6;
$R_6$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from: halogen, cyano, $C_{1-4}$alkyl, halo$C_{1-4}$alkyl, $C_{1-4}$alkoxy, $C_{1-4}$alkanoyl;
$R_4$ is selected in the group consisting of: hydrogen, halogen, hydroxy, cyano, $C_{1-4}$alkyl, $C_{3-7}$ cycloalkyl, halo$C_{1-4}$alkyl, $C_{1-4}$alkoxy, halo$C_{1-4}$alkoxy, $C_{1-4}$alkanoyl and NR'R"; or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, halo$C_{1-4}$alkoxy and $SF_5$;
$R_7$ is hydrogen or $C_{1-2}$alkyl;
R' is H, $C_{1-4}$ alkyl or $C_{1-4}$ alkanoyl;
R" is defined as R';
R' and R" taken together with the interconnecting nitrogen atom may form a 5-, 6-membered saturated or unsaturated heterocyclic ring.

Because of the presence of the fused cyclopropane, compounds of formula (I) are believed to have a "cis" disposition of the substituents (both groups linked to the bicyclic ring system are on the same face of this bicyclic ring system).

In one embodiment of the present invention compounds of formula (I)' are provided which correspond to the compounds of formula (I), or salts thereof, having "cis" disposition, represented by the bold highlight of the bonds

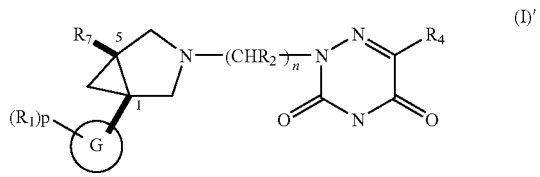

(I)' wherein G, p, n, $R_1$, $R_2$, $R_4$ and $R_7$ are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration); through optical resolution of a mixture containing the two stereoisomers which are enantiomers with respect to the chiral centres in the cyclopropane, single steroisomers of compounds of formula (I)' may be obtained as shown in the scheme below:

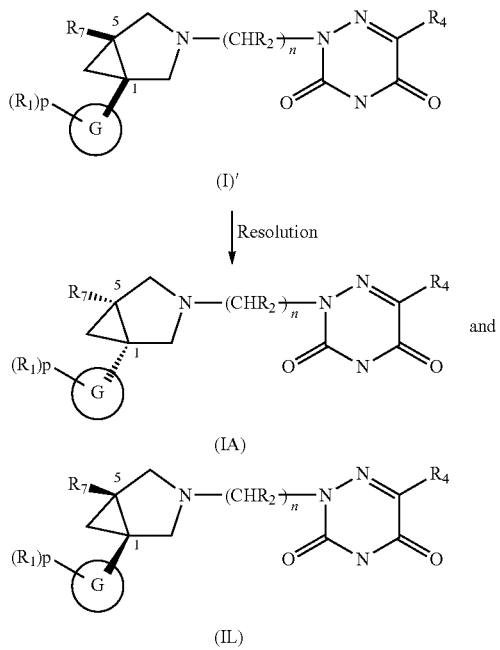

Absolute configuration of chiral center at position named 1 and 5 may be assigned using Cahn-Ingold-Prelog nomenclature based on groups' priorities.

In one embodiment of the present invention compounds of formula (IA) are provided that correspond to stereochemical isomers of compounds of formula (I)', enriched in configuration shown in the picture below at chiral centers at position named 1 and 5:

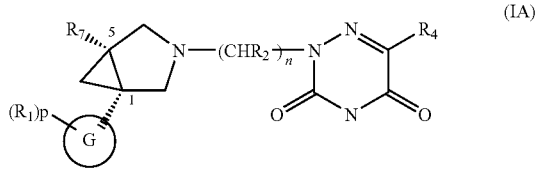

(IA)

wherein G, p, n, $R_1$, $R_2$, $R_4$ and $R_7$ are defined as above for compounds of formula (I), or a salt thereof.

It is intended in the context of the present invention that stereochemical isomers of formula (IA) enriched in one configuration at centers named 1 and 5, correspond in one embodiment to at least 90% e.e. (enantiomeric excess). In another embodiment the isomers correspond to at least 95% e.e. In another embodiment the isomers correspond to at least 99% e.e.

In another embodiment of the present invention compounds of formula (IH) are provided that correspond to stereochemical isomers of compounds of formula (I)', enriched in configuration (1S,5R) or (1R,5R)

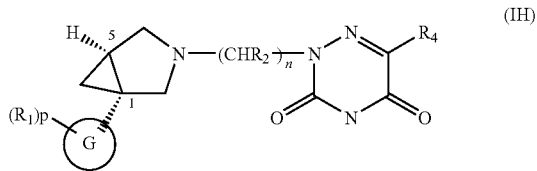

(IH)

wherein G, p, n, $R_1$, $R_4$ and $R_2$ are defined as above for compounds of formula (I) and $R_7$ is hydrogen, or a salt thereof.

Different nomenclature for absolute configuration assigned to chiral center named 1 [(1R) or (1S)] may be generated by different meanings for G group.

For example, when the group G is a phenyl group, absolute configuration nomenclature for compounds of formula (IH) is (1S,5R).

It is intended in the context of the present invention that stereochemical isomers enriched in configuration (1S,5R) or (1R,5R) of formula (IH) correspond in one embodiment to at least 90% e.e. (enantiomeric excess). In another embodiment the isomers correspond to at least 95% e.e. In another embodiment the isomers correspond to at least 99% e.e.

In another embodiment of the present invention the stereochemical isomers enriched in configuration (1R,5S) are provided.

In another embodiment of the present invention compounds of formula (IL) are provided that correspond to stereochemical isomers of compounds of formula (I)', enriched in configuration shown in the picture below at chiral centers at position named 1 and 5:

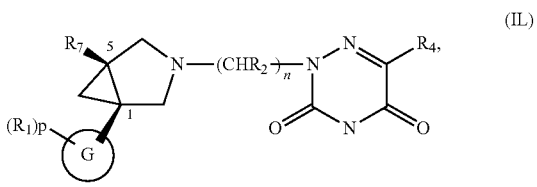

(IL)

wherein G, p, n, $R_1$, $R_4$, $R_2$ and $R_7$ are defined as above for compounds of formula (I), or a salt thereof.

The term '$C_{1-4}$ alkyl' as used herein as a group or a part of the group refers to a linear or branched alkyl group containing from 1 to 4 carbon atoms; examples of such groups include methyl, ethyl, propyl, isopropyl, n-butyl, isobutyl, tert butyl.

The term '$C_{3-7}$ cycloalkyl group' as used herein means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term '$C_{1-4}$ alkoxy group' as used herein may be a linear or a branched chain alkoxy group, for example methoxy, ethoxy, propoxy, prop-2-oxy, butoxy, but-2-oxy or methyl-prop-2-oxy and the like.

The term '$C_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term 'halogen' as used herein refers to a fluorine, chlorine, bromine or iodine atom.

The term 'halo $C_{1-4}$ alkyl' as used herein means an alkyl group having one or more carbon atoms and wherein at least one hydrogen atom is replaced with halogen such as for example a trifluoromethyl group and the like.

The term 'halo $C_{1-4}$ alkoxy group' as used herein may be a $C_{1-4}$ alkoxy group as defined before substituted with at least one halogen, preferably fluorine, such as $OCHF_2$, or $OCF_3$.

The term 'aryl' as used herein means an aromatic carbocyclic moiety such as phenyl, biphenyl or naphthyl.

The term '5,6-membered monocyclic heteroaryl' as used herein means an aromatic monocyclic heterocycle ring of 5 or 6 members and having at least one heteroatom selected from nitrogen, oxygen and sulfur, and containing at least 1 carbon atom.

Representative 5, 6 membered monocyclic heteroaryl groups include (but are not limited to): furyl, thiophenyl, pyrrolyl, pyridyl, oxazolyl, isooxazolyl, pyrazolyl, imidazolyl, thiazolyl, isothiazolyl, pyridazinyl, pyrimidinyl, pyrazinyl, triazinyl, triazolyl and tetrazolyl.

The term '8,11-membered bicyclic heteroaryl' as used herein means an aromatic bicyclic heterocycle ring of 8 to 11 members and having at least one heteroatom selected from nitrogen, oxygen and sulfur, and containing at least 1 carbon atom.

Representative 8, to 11 membered bicyclic heteroaryl groups include (but are not limited to): benzofuranyl, benzothiophenyl, indolyl, isoindolyl, azaindolyl, quinolinyl, isoquinolinyl, benzoxazolyl, benzimidazolyl, benzothiazolyl, quinazolinyl and phthalazinyl.

The term 5-14 membered heterocycle means a 5 to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a physiologically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

In one embodiment, $R_1$ is halogen, cyano, acetyl, trifluoromethyl or trifluoromethoxy.

In another embodiment, $R_1$ is trifluoromethyl.

In one embodiment, $R_2$ is hydrogen. In another embodiment $R_2$ is $C_{1-4}$ alkyl (e.g. methyl).

In one embodiment $R_4$ is hydrogen, $C_{1-4}$alkyl, halo$C_{1-4}$alkyl, $C_{1-4}$alkoxy, halo$C_{1-4}$alkoxy, $C_{1-4}$alkanoyl, halogen, phenyl or hydroxy.

In another embodiment $R_4$ is hydrogen, $C_{1-4}$alkyl (for example methyl), halogen (for example fluorine), halo$C_{1-4}$alkyl (for example trifluoromethyl), an optionally substituted 5-14 membered heterocycle (for example optionally substituted thiophenyl, pyrrolidinyl, pyridinyl, isoxazolyl, pyridazinyl, oxazolyl, pyrazinyl), optionally substituted phenyl, cyano or $C_{3-7}$ cycloalkyl (for example cyclopropyl).

In a further embodiment, $R_4$ is an optionally substituted phenyl or 5,6-membered heteroaryl group (for example optionally substituted thiophenyl, pyridinyl, isoxazolyl, pyridazinyl, oxazolyl, pyrazinyl).

In one embodiment, $R_6$ is a group selected from: isoxazolyl, 2-pyrrolidinonyl, —$CH_2$—N-pyrrolyl, 1,1-dioxido-2-isothiazolidinyl, 2-thienyl, 2-pyridyl, 2-thiazolyl which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy), $C_{1-3}$alkanoyl (e.g. acetyl).

In one embodiment, G is phenyl.

In one embodiment $R_7$ is hydrogen or methyl.

In another embodiment $R_7$ is hydrogen.

In one embodiment, p is 0, 1 or 2.

In another embodiment, p is 1.

In one embodiment, n is 3 or 4.

In another embodiment, $R_4$ is hydrogen, methyl, hydroxy, phenyl or fluorine.

In another embodiment, $R_6$ is isoxazolyl, 2-pyrrolidinonyl, -1,1-dioxido-2-isothiazolidinyl.

In another embodiment, $R_7$ is hydrogen.

In another embodiment, p is 1 and $R_1$ is trifluoromethyl.

In one embodiment, a compound of formula (IB) or a salt thereof is provided, wherein $R_1$, $R_2$, $R_4$, p, n and $R_7$ are as defined for formula (I):

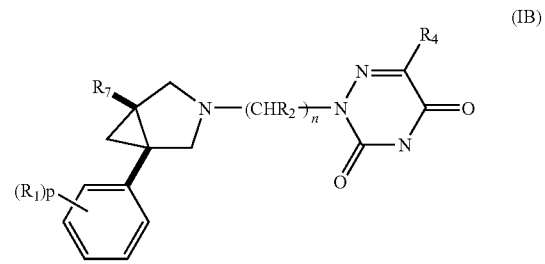

(IB)

In Formula (IB), in one embodiment, n is 3 or 4, p is 1, $R_1$ is trifluoromethyl, $R_2$ is hydrogen, $R_4$ is hydrogen, methyl, hydroxy, fluorine or an optionally substituted phenyl or 5,6-membered heteroaryl group and $R_7$ is hydrogen.

The absolute configuration of the compounds of the present invention was may be assigned in agreement with the method described in the PCT International Publication WO2005/080382.

In one embodiment, a stereochemical isomer of formula (IB)' or a salt thereof is provided, enriched in the configuration shown in the picture below at chiral centers at position named 1 and 5, wherein $R_1$, $R_2$, $R_4$, p, n, and $R_7$ are as defined for formula (I):

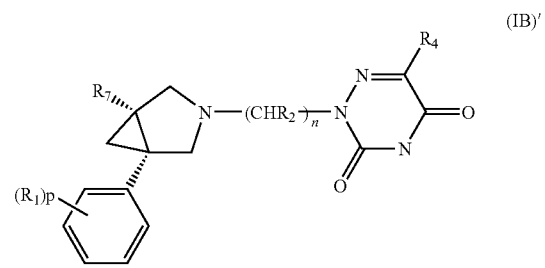

(IB)'

In Formula (IB)', in one embodiment, n is 3 or 4, p is 1, $R_1$ is trifluoromethyl, $R_2$ is hydrogen, $R_4$ is hydrogen, methyl, hydroxyl, fluorine or an optionally substituted phenyl or 5,6-membered heteroaryl group and $R_7$ is hydrogen.

In a further embodiment, a stereochemical isomer enriched in the (1S,5R) configuration of formula (IM) or a salt thereof is provided, wherein $R_4$ and n are as defined for formula (I):

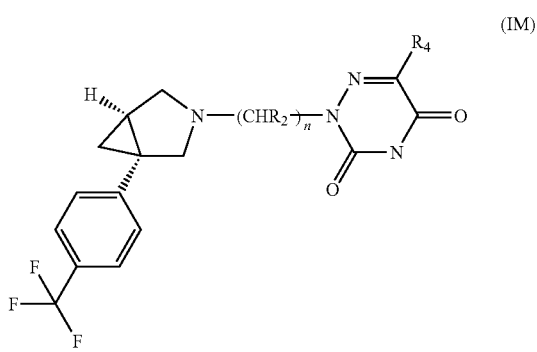

(IM)

In Formula (IM), in one embodiment, n is 3 or 4, p is 1 and $R_4$ is an optionally substituted phenyl or 5,6-membered heteroaryl group (for example optionally substituted thiophenyl, pyridinyl, isoxazolyl, pyridazinyl, oxazolyl, pyrazinyl).

Example compounds of the invention include:

6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-(2-methyl-4-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-(2-methyl-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-(2-fluoro-3-pyridinyl)-2-(3-{1-methyl-5-[4-(trifluoromethyl)phenyl]-3-azabicyclo[3.1.0]hex-3-yl}propyl)-1,2,4-triazine-3,5(2H,4H)-dione (Enantiomer 2);

2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-phenyl-2-(3-{(1S,5R)-1-[4-(trifluoromethyl)phenyl]-3-azabicyclo[3.1.0]hex-3-yl}propyl)-1,2,4-triazine-3,5(2H,4H)-dione;

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione; or salts thereof.

Certain of the compounds of the invention may form acid addition salts with one or more equivalents of the acid. The present invention includes within its scope all possible stoichiometric and non-stoichiometric forms.

Pharmaceutically acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) or salts thereof, may exist as polymorphs, which are included in the present invention.

Hereinafter, compounds of formula (I) and their pharmaceutically acceptable salts, solvates and prodrugs defined in any aspect of the invention (except intermediate compounds in chemical processes) are referred to as "compounds of the invention".

Those skilled in the art will appreciate that in the preparation of the compounds of the invention, it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}C$, $^{18}C$, $^{31}P$, $^{32}P$, $^{35}S$, $^{18}F$, $^{36}Cl$, $^{123}I$ and $^{125}I$.

Compounds of the present invention and non-pharmaceutically acceptable salts thereof that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and non-pharmaceutically acceptable salts thereof can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

It will be appreciated by the person skilled in the art that compounds of formula (I) may exist in the tautomeric forms (IC) and (ID) as below described:

with a compound of formula (III):

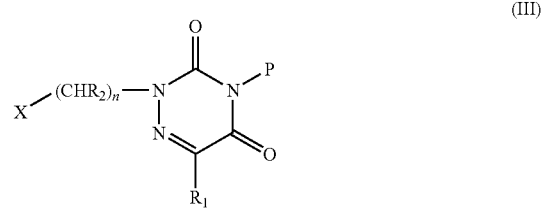

wherein $R_1$, $R_2$ and n are as defined for formula (I) and X is a leaving group and P is a suitable nitrogen protecting group; e.g. benzoyl protecting group.

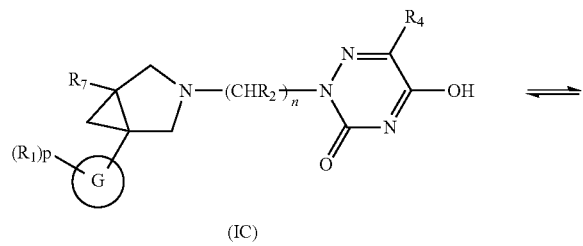

Both tautomeric forms are intended to be included within the scope of this invention.

Some of the compounds of the present invention may be prepared following some of the procedures described in PCT International Publication WO2005/080382.

The present invention also provides a process for preparing a compound of formula (I)' or a salt thereof as defined above, which comprises the steps of:

a) reacting a compound of formula (II):

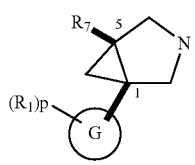

Or b) reacting a compound of formula (II) as above defined with a compound of formula (IV)

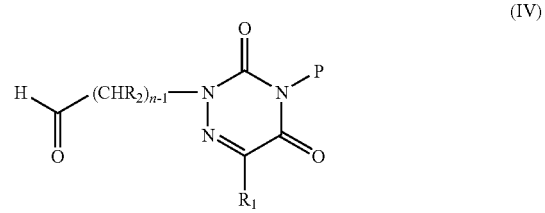

wherein $R_1$, $R_2$ and n are as defined for formula (I) and P is a suitable nitrogen protecting group;
and thereafter optionally for process (a) or process (b):
(i) removing any protecting group(s); and/or
(ii) forming a salt; and/or
(iii) converting a compound of formula (I)' or a salt thereof to another compound of formula (I)' or a salt thereof.

Process (a) may be performed using conventional methods for the formation of a tertiary amine. The leaving group X can be halogen such as chlorine. Alternatively X can be a sulfonyloxy group such $C_{1-4}$alkylsulfonyloxy (e.g. methanesulfo nyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Process (b) may be performed using conventional methods for the formation of a tertiary amine by means of reductive ammination. For example the reaction may be carried out using sodium triacetoxy borohydride in a suitable solvent such as 1,2 dichloroethane or acetonitrile at 0° C.

Compounds of formula (II) may be prepared by methods well known in the art (e.g. *J. Med. Chem.* 1981, 24, 481-490 or PCT International Publication WO2005/080382).

A compound of formula (III) as above defined may itself be prepared by reacting a compound of formula (V):

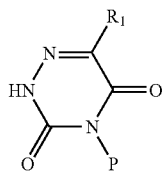

(V)

wherein $R_1$ is as hereinbefore defined for formula (I) and P is a suitable nitrogen protecting group, such as benzyl or benzoyl derivative with a compound of formula (VI):

LCH$_2$(CH$_2$)$_n$CH$_2$X    (VI)

wherein n is defined as for formula (I), X is as defined above for compounds of formula (III) and L is a leaving group, e.g., a bromine atom.

Alternatively L can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

A compound of formula (IV) as above defined may be prepared by:
f) reacting a compound of formula (V) as above defined:

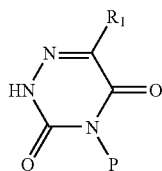

(V)

with a compound of formula (VII):

MCH(CHR$_2$)$_{n-1}$X    (VII)

wherein n is defined as for formula (I), X is as defined above for compounds of formula (III) and M is an appropriate carbonylic protecting group (for example dimethylacetale or dioxolane);

and then g) cleavage of the protecting group/s.

Cleavage of the protecting groups may be carried out under appropriate conditions known to the man skilled in the art. For example, when M is dimethylacetale and P is benzoyl derivative, the cleavage may carried out by treatment with a diluted solution of hydrochloric acid in dioxane or methanol under gentle heating (e.g. 60° C.).

A compound of formula (IV), as above defined, may also be prepared by:
h) reacting a compound of formula (V), as above defined:

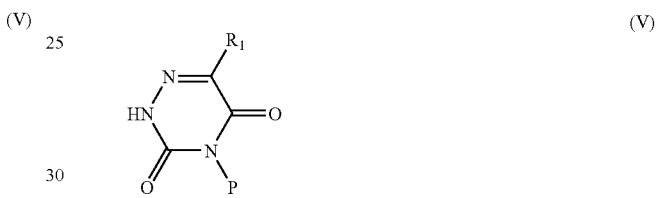

(V)

with a compound of formula (VIII)

NCH$_2$(CHR$_2$)$_{n-1}$X    (VIII)

wherein n is defined as for formula (I), X is as above defined and N is a protected alcoholic function (for example: terbutyldimethylsilyl) to form a compound of formula (IX)

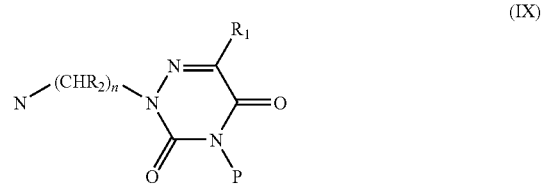

(IX)

and then i) cleavage of the nitrogen protecting group under appropriate conditions known to the man skilled in the art ii) cleavage of the oxygen protecting group under appropriate conditions known to the man skilled in the art and subsequent oxidation of the free alcoholic function obtained to carbonyl group.

For example when P is a benzoyl group the cleavage can be performed by treatment with diluted ammonia in metanolic solution at room temperature. Then, when N is a terbutyl dimethyl silyl protecting group the cleavage can be performed by treatment with a 1N solution of hydrochloric acid in dioxane at 0° C. for 1 hour. Appropriate conditions for the oxidation step comprise Dess-Martin periodinane mediated oxidation in dry THF as solvent at 0° C. for 1 hour.

A compound of formula (IVa), which is a compound of formula (IV) as above defined wherein n=1, may also be prepared by:

h) reacting a compound of formula (V), as above defined:

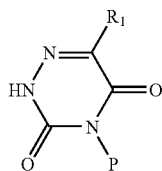

with a compound of formula (XXII)

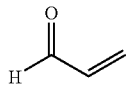

By means of azaMichael reaction. Typical reaction conditions may comprise the use of N,N-DMF as solvent and TEA as base at room temperature.

Compounds of formula (V):

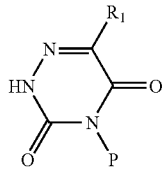

wherein $R_1$ is defined as for compounds of formula (I) and P is a suitable nitrogen protecting group may be prepared from compound of formula (X)

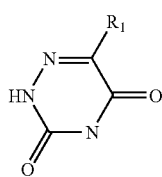

through reactions known in the literature or through the procedures herebelow described.

For example, compounds of formula (V) may be prepared according to the following process:

c) by protecting the N5 nitrogen in compounds of formula (XI) wherein $R_1$ is defined as for compounds of formula (I) and P1 is a suitable nitrogen protecting group

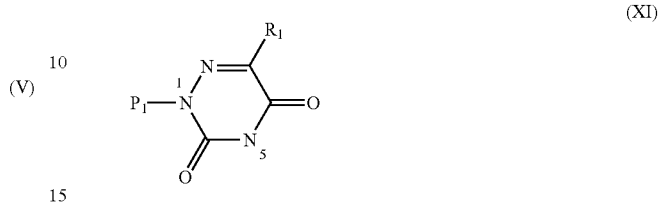

to give compounds of formula (XII)

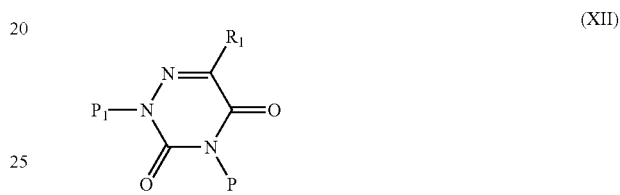

For example, when P is a benzoyl protecting group compounds (XI) are dissolved in dry pyridine at 0° C. and benzoylchloride added dropwise.

d) followed by the cleavage of the P1 protecting group.

For example when P1 is acetyl protecting group and P is a benzoyl group the cleavage of the former group can be performed using a diluted solution of hydrochloric acid at reflux temperature for 15 min.

Compounds of formula (XI):

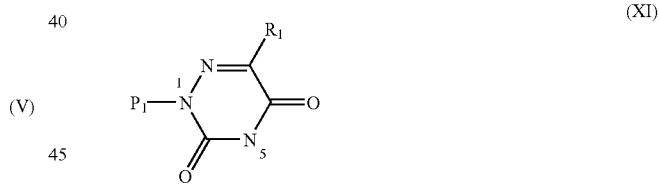

may be prepared from commercially available compounds through reactions known in the literature.

When a specific enantiomer or diastereoisomer of a compound of formula (I) or salts thereof, is required, this may be obtained for example by resolution of a corresponding enantiomeric or diastereosiomeric mixture using conventional methods.

Thus, for example, specific enantiomers or diastereoisomers of the compounds may be obtained from the corresponding enantiomeric or diastereoisomeric mixture using chiral chromatographic methods such as for example chiral HPLC.

Alternatively a specific enantiomer or diastereoisomer of a compound of general formula (I), or salts thereof, may be synthesised from the appropriate optically active intermediates using any of the general processes described herein.

Compounds of formula (I) or pharmaceutically acceptable salts thereof, have been found to exhibit affinity for dopamine receptors, in particular the $D_3$ receptor, and are expected to be useful in the treatment of disease states which require modulation of such receptors, such as psychotic conditions.

Many of the compounds of formula (I) or pharmaceutically acceptable salts thereof have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of formula (I) or salts thereof are provided which have higher (e.g. $\geq 10\times$ or $\geq 100\times$ higher) affinity for dopamine $D_3$ than dopamine $D_2$ receptors (such affinity can be measured using standard methodology—see herein).

Compounds of the invention may suitably be used as selective modulators of $D_3$ receptors. From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include substance related disorders, dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, amnesia, aggression, vertigo, dementia, circadian rhythm disorders and gastric motility disorders e.g. IBS.

Compounds of formula (I) will be used for treatment of all aspects of drug dependency including prevention of relapse to and relief of withdrawal symptoms from drugs of abuse such as nicotine, alcohol, cocaine, amphetamine, metamphetamine, opiates, benzodiazepines, inhalants and inhibition of tolerance induced by opioids. In addition, compounds of formula (I) and pharmaceutically acceptable salts and solvates thereof will be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the maintenance of drug dependence and the probability of relapse or reinstatement of drug seeking and drug taking behaviors.

A wide range of psychiatric and neuropsychiatric disorders appear to be related to Obsessive-Compulsive Disorder, and form a family of related disorders referred to as obsessive-compulsive (OC) spectrum disorders. The compounds of the invention may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of the invention are also useful for the treatment of premature ejaculation.

The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

The term "psychotic disorder" includes:
Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term "substance-related disorder" includes:
Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Compounds of the invention may be useful for the treatment of cognition impairment.

The term "cognition impairment" includes cognition impairment in other diseases such as schizophrenia, bipolar disorder, depression, other psychiatric disorders and psychotic conditions associated with cognitive impairment, e.g. Alzheimer's disease.

Within the context of the present invention, it is intended that the expression "treatment of a substance-related" disorder also includes prevention of relapse into such substance related-disorder.

In a further aspect therefore the present invention provides a method of treating a condition for which modulation of dopamine receptors (especially dopamine $D_3$ receptors) is beneficial, which comprises administering to a mammal (e.g. human) in need thereof an effective amount of a compound of the invention.

Modulation, as used herein, especially refers to inhibition/antagonism (which may also translate into inverse agonism in constitutively active receptor systems).

In one embodiment, the condition is a substance-related disorder, a psychotic disorder, an obsessive compulsive spectrum disorder or premature ejaculation.

In one embodiment, the substance-related disorder is nicotine dependence.

The invention also provides a compound of the invention for use in therapy.

The invention also provides a compound of the invention for use in the treatment of a condition in a mammal for which modulation of dopamine receptors (especially dopamine $D_3$ receptors) is beneficial.

The invention also provides the use of a compound of the invention in the manufacture of a medicament for the treatment of a condition in a mammal for which modulation of dopamine receptors (especially dopamine $D_3$ receptors) is beneficial.

In one embodiment, compounds of the invention are used in the treatment of psychoses such as schizophrenia, in the treatment of substance related disorders, in the treatment of obsessive compulsive spectrum disorders, in the treatment of premature ejaculation.

Also provided is the use of a compound of the invention in the manufacture of a medicament for the treatment of a psychotic condition, substance-related disorders in a mammal, obsessive compulsive spectrum disorders, and premature ejaculation.

Also provided is a compound of the invention for use in the treatment of a psychotic condition (e.g. schizophrenia), substance-related disorders, obsessive compulsive spectrum disorders, and premature ejaculation in a mammal.

Also provided is a compound of the invention or for use as an active therapeutic substance in a mammal, e.g. for use in the treatment of any of the conditions described herein.

In one embodiment, the mammal is a human.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of the invention and a pharmaceutically acceptable carrier. The pharmaceutical composition can be for use in the treatment of any of the conditions described herein.

Compound of the invention may be administered by any convenient method, for example by oral, parenteral (e.g. intravenous), buccal, sublingual, nasal, rectal or transdermal administration and the pharmaceutical compositions adapted accordingly.

Compound of the invention which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the invention calculated as the free base.

The compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency of compounds of this invention can be measured by the following GTPγS scintillation proximity assay (GTPγS-SPA). Cells used in the study are Chinese Hamster Ovary (CHO) Cells for D3 and Chinese Hamster Ovary (CHO) or Human Embryonic Kidney (HEK) cells for D2.

Cell Line

CHO_D2 or HEK_D2

CHO_D3

Dopamine CHO $D_3$ transduced with bacmam G0 G-protein.

All steps are performed at 4° C. Cell membranes are prepared as follows. Cell pellets are resuspended in 10 volumes of 50 mM HEPES, 1 mM EDTA pH 7.4, using KOH.

Cells are homogenised within a glass waring blender for 2 bursts of 15 secs in 200 mls of buffer (50 mM HEPES, 1 mM leupeptin, 25 m/ml bacitracin, 1 mM EDTA, 1 mM PMSF, 2 μM Pepstatin A). (the latter 2 reagents added as fresh ×100 and ×500 stocks respectively in ethanol). The blender is plunged into ice for 5 mins after the first burst and 10-40 mins after the final burst to allow foam to dissipate. The material is then spun at 500 g for 20 mins and the supernatant spun for 36 mins at 48,000 g. The pellet is resuspended in the same buffer as above but without PMSF and Pepstatin A. The material is then forced through a 0.6 mm needle, made up to the required volume, (usually ×4 the volume of the original cell pellet), aliquoted and stored frozen at −80° C.

The final top concentration of test drug is 3 μM in the assay and 11 points serial dilution curves 1:4 in 100% DMSO are carried out using a Biomek FX. The test drug at 1% (0.5 ul) total assay volume (TAV) is added to a solid, white Greiner polypropylene 384-well assay plate. 50% TAV (25 μl) of precoupled (for 60 mins at RT) membranes, 5 μg/well, and Wheatgerm Agglutinin Polystyrene Scintillation Proximity Assay beads (RPNQ0260, Amersham), 0.25 mg/well, in 20 mM HEPES (pH 7.4, 100 mM NaCl, 10 mM MgCl2), 60 μg/mL saponin and 3 uM for D2 and 30 uM for D3 GDP is added. The third addition is a 20% TAV (10 ul) addition of either buffer, (agonist format) or EC80 final assay concentration of agonist, Quinelorane, prepared in assay buffer (antagonist format). The assay is started by the addition of 29% TAV (15 ul) of GTP[35S] 0.38 nM final (37 MBq/mL, 1160 Ci/mmol, Amersham). After all additions assay plates are spun down for 1 min at 1,000 rpm. The final assay cocktail (50.5 μl) is incubated at room temperature to equilibrate for 3-6 hours before reading on a ViewLux™ (613/55 filter) luminescence imager 5 min/plate.

The effect of the test drug over the basal generates fpKi values of test drug are calculated from the $IC_{50}$ generated by "antagonist format" experiment, using Cheng & Prusoff equation: $fKi=IC50/1+([A]/EC50)$ where: [A] is the concentration of the agonist Quinelorane in the assay and EC50 is the Quinelorane EC50 value obtained in the same experiment. fpKi is defined as −log fKi.

pKi results are only estimated to be accurate to about 0.3-0.5.

In the context of the present invention functional pKi (fpKi, corresponding to the negative logarithm of fKi) is used instead of functional Ki (fKi) and the compounds of formula (I) and salts thereof typically show fpKi for D3 receptors higher than 7.0.

In one embodiment compounds of formula (I) or salts thereof are provided which have higher affinity for dopamine $D_3$ than dopamine $D_2$ receptors.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar or analogous" procedure, as will be appreciated by those skilled in the art, such a procedure may involve minor variation, for example reaction temperature, reagent/solvent amount, reaction time, work-up conditions or chromatographic purification conditions.

All temperatures refer to ° C.

Proton Magnetic Resonance (NMR) spectra may be typically recorded either on Varian instruments at 300, 400 or 500 MHz, or on a Bruker instrument at 300 and 400 MHz.

Chemical shifts are expressed in parts per million (ppm, δ units). Coupling constants are in units of hertz (Hz) chemical shifts are reported in ppm downfield (d) from $Me_4Si$, used as internal standard, and are typically assigned as singlets (s), broad singlets (bs), doublets (d), doublets of doublets (dd), triplets (t), quartets (q) or multiplets (m).

Mass spectra (MS) may be typically taken on a 4 II triple quadrupole Mass Spectrometer (Micromass UK) or on a Agilent MSD 1100 Mass Spectrometer, operating in ES (+) and ES (−) ionization mode or on an Agilent LC/MSD 1100 Mass Spectrometer, operating in ES (+) and ES (−) ionization mode coupled with HPLC instrument Agilent 1100 Series. In the mass spectra only one peak in the molecular ion cluster is typically reported.

LCMS may be recorded under the following conditions:
DAD chromatographic traces, mass chromatograms and mass spectrums may be taken on a HPLC/MS Acquity™ system coupled with a Micromass ZQ™ mass spectrometer operating in ESI positive. The phases used are: A) H2O/ACN 95/5+0.1% TFA; B) H2O/ACN 5/95+0.1% TFA. The gradient is: t=0 min) 95% A 5% B, t=0.25) 95% A 5% B, t=3.30) 100% B, t=4.0) 100% B, followed by 1 min of reconditioning
Column: Acquity BEH C18 2.1×50 mm 1.7 um 35° C. Flow: 600 uL/min.
Mass tune: Capillary 3.25 kV, cone 20V, source temperature 115° C. desolvation T 350° C.

Unless otherwise specified, Preparative LC-MS purifications may be performed under the following conditions:
Instrument: HPLC-MS preparative system Waters (2767 and 2525) coupled with photodiode array detector and Micromass ZQ. Column: Waters XTerra MS C18 (19×300 mm, 10 um). Flow rate 20 ml/min. Mobile phase: A phase=water+0.1% TFA, B phase=acetonitrile+0.1% TFA. 0-3.0 min (A: 90%, B: 10%), 3.0 min (A: 90%, B: 10%), 3.0-26.0 min (A: 5%, B: 95%), 26.0 min (A: 5%, B: 95%), 26.0-30.0 min (A: 5%, B: 95%), 30.0 min (A: 5%, B: 95%), 30.0-30.5 min (A: 90%, B: 10%), 30.5 min (A: 90%, B: 10%), 30.5-31.5 min (A: 90%, B: 10%). The fractions containing the pure material are typically collected and the solvents evaporated. The so obtained trifluoroacetate salts are typically neutralized by passing over SCX cartridge.

Unless otherwise specified, Preparative "LC-MS conditions—basic method" may be: Column: Gemini C18 AXIA, 50×21 mm, 5 μm; Mobile phase: A: NH4HCO3 sol. 10 mM, pH10; B: CH3CN; Gradient: 35% (B) for 1 min, 35% to 45% (B) in 9 min, 45% to 100% (B) in 2 min, 100% (B) for 1.5 min; Flow rate: 17 ml/min; UV range: 210-350 nm; Ionization: ES+; Mass range: 100-900 amu. The so obtained fraction are typically evaporated to give the compound as free base.

Preparative HPLC purifications may be performed under the following conditions:
Instrument: Shimadzu (LC/8A and SCL/10A) coupled with UV spectrophotometric dector (SPD/6A). Column: Waters SymmetryPrep C18 19×30 mm×7 um; flow rate: 20 ml/min; mobile phase: A phase=water/acetonitrile 9/1+0.5% TFA, B phase=water/acetonitrile 5/95+0.5% TFA using a 30 min gradient of 5-100% solvent B.

The fractions containing the pure material are typically collected and the solvents evaporated. The so obtained trifluoroacetate salts are typically neutralized by passing over SCX cartridge.

Preparative HPLC purifications (FractionLynx) may be performed under the following conditions:
MDAP FractionLynx Autopurification System™ Waters
Column: SUPELCOSIL ABZ+Plus, 100×21.2 mm, 5 μm ps
Mobile phase: A: H2O+0.1% HCOOH; B: $CH_3CN$+0.1% HCOOH
Gradient: t=0 min 5% (B) in 1 min, 5% to 95% (B) in 9 min, 95% to 100% (B) in 3 min
Flow rate: 20 ml/min
UV range: 210-400 nm
Ionization: ES+/ES−
Mass range: 150-900 da Optical rotations may be typically measured using a (Perkin Elmer Model 341) polarimeter operating at 589 nm (Sodium source) [Measurements are made using a 1 decimeter microcell thermostated at 23° C. Concentrations are typically 10 mg/ml (c=1)] or using a (Perkin Elmer Model 241) polarimeter operating at 589 nm (Sodium source) [Measurements are made using a 1 decimeter microcell thermostated at 23° C. Concentrations are typically 10 mg/mL (c=0.01)]. For ab initio OR assignments, the Dalton Quantum Chemistry Program are used.

Melting point determination may be performed on a Buchi B-540 apparatus.

Compounds may be named using ACD/Name PRO6.02 chemical naming software (Advanced Chemistry Development Inc., Toronto, Ontario, M5H2L3, Canada) or ISIS/Draw 2.5 SR 2 Autonom (MDL Information System, Inc)

For reactions involving microwave irradiation, a Personal Chemistry Emrys™ Optimizer may be used.

Flash silica gel chromatography may be carried out on silica gel 230-400 mesh (supplied by Merck AG Darmstadt, Germany) or over pre-packed Biotage silica cartridges.

Purification may also be performed using either Biotage manual flash chromatography (Flash+). All these instruments work with Biotage Silica cartridges.

Unless otherwise stated, all reaction are typically performed under inert atmosphere (for example under Nitrogen).

The following abbreviations are used in the text: EtOAc, AcOEt=ethyl acetate, $Et_2O$=diethyl ether, MeOH=methanol; THF=tetrahydrofuran, Tlc refers to thin layer chromatography on silica plates, and dried refers to a solution dried over anhydrous sodium sulphate, r.t. (RT) refers to room temperature, DMSO=dimethyl sulfoxide; DMF=N,N'-dimethylformamide, DCM=dichloromethane, EtOH=ethanol; DCE=dichloroethane, cy=cyclohexane; SPE Cartridge=Solid Phase Extraction Cartridge; SCX Cartridge=Strong Cation Exchange Cartridge.

Preparation 1: 2-acetyl-6-methyl-1,2,4-triazine-3,5 (2H,4H)-dione (P1)

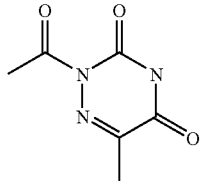

6-azathymine (commercially available from Alfa Aesar, 300 mg, 2.360 mmol), was suspended in acetyc anhydride (1.34 mL, 14.20 mmol) and the mixture was refluxed for 2 hours. The reaction mixture was then cooled to room temperature and dried under vacuum. The crude product was repeatedly treated with toluene and concentrated under reduced pressure to afford the title compound 2-acetyl-6-methyl-1,2,4-triazine-3,5(2H,4H)-dione that was used for next step without purification.

MS (ES) (m/z): 170.06 [M+H]$^+$.

Preparation 2: 6-methyl-4-(phenylcarbonyl)-1,2,4-triazine-3,5(2H,4H)-dione (P2)

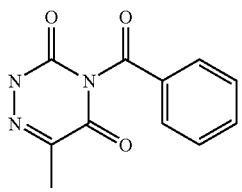

To a solution of 2-acetyl-6-methyl-1,2,4-triazine-3,5(2H, 4H)-dione (P1, 196 mg, 1.159 mmol) in 1,4-Dioxane (2 mL) and dry pyridine (0.281 mL, 3.48 mmol) at 5° C. was treated benzoyl chloride (0.155 mL, 1.333 mmol) was added dropwise, then the mixture was stirred at room temperature overnight. The day after 0.1 eq of Benzoyl chloride were added and the mixture stirred at rt for further 4 hours. The reaction mixture was then filtered to remove the piridinium salt and the solvents evaporated under vacuum. The residue was dissolved in EtOH (5 mL), then HCl 37% (126 µL) was added and the reaction was refluxed for 15 minutes. Solvent was evaporated under reduced pressure and the residue was purified by flash chromatography (eluent: DCM to DCM/MeOH 6:4) providing the title compound 6-methyl-4-(phenylcarbonyl)-1,2,4-triazine-3,5(2H,4H)-dione (180 mg, 0.779 mmol, 67% yield).

MS (ES) (m/z): 232.11 [M+H]$^+$.

Preparation 3: 2-[3,3-bis(methyloxy)propyl]-6-methyl-4-(phenylcarbonyl)-1,2,4-triazine-3,5(2H,4H)-dione (P3)

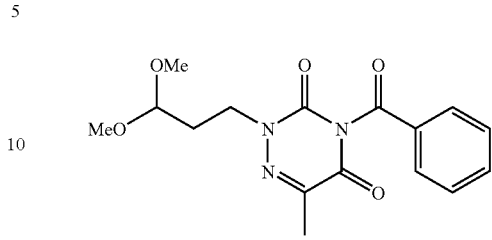

To a solution of 6-methyl-4-(phenylcarbonyl)-1,2,4-triazine-3,5(2H,4H)-dione (P2, 90 mg, 0.389 mmol) in N,N-Dimethylformamide (DMF) (0.6 mL), potassium carbonate (64.6 mg, 0.467 mmol) and 3-bromo-1,1-bis(methyloxy)propane (commercially available from Aldrich, 0.071 mL, 0.467 mmol), were added and the mixture was stirred at rt overnight. The day after the reaction mixture was quenched with water and diluted with AcOEt. Organic phase was washed with water and brine, dried over Na$_2$SO$_4$ and evaporated under reduced pressure. Crude product was purified by flash chromatography (Cy 100% to Cy/AcOEt 6:4) affording the title compound 2-[3,3-bis(methyloxy)propyl]-6-methyl-4-(phenylcarbonyl)-1,2,4-triazine-3,5(2H,4H)-dione (92 mg, 0.276 mmol, 70.9% yield) as a clear oil.

MS (ES) (m/z): 356.08 [M+Na]$^+$.

Preparation 4: 6-methyl-4-(phenylcarbonyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (P4)

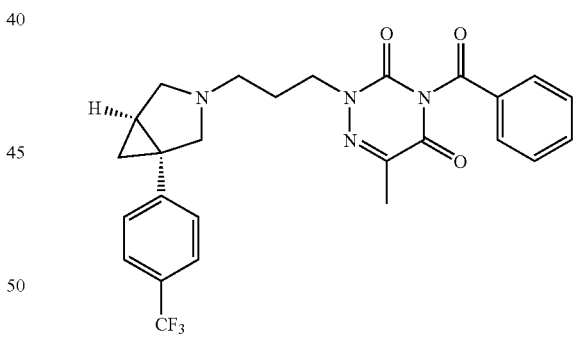

Step a:

To a solution of 2-[3,3-bis(methyloxy)propyl]-6-methyl-4-(phenylcarbonyl)-1,2,4-triazine-3,5(2H,4H)-dione (P3, 92 mg, 0.276 mmol) in Tetrahydrofuran (THF) (2.3 mL), 1N hydrochloric acid aqueous solution (0.690 mL, 0.690 mmol) was added and the mixture was stirred at rt for 2.5 hours. The reaction was then quenched with water and extracted with AcOEt. Organic phase was washed with water and NaHCO$_3$ saturated solution, dried over Na2SO4 and evaporated under reduced pressure affording 3-[6-methyl-3,5-dioxo-4-(phenylcarbonyl)-4,5-dihydro-1,2,4-triazin-2(3H)-yl]propanal as a crude product that was used for next step without purification.

Step b:
3-[6-methyl-3,5-dioxo-4-(phenylcarbonyl)-4,5-dihydro-1,2,4-triazin-2(3H)-yl]propanal, Titanium (IV) isopropoxide (0.110 mL, 0.376 mmol) and (1S,5R)-1-[4-(trifluoromethyl)phenyl]-3-azabicyclo[3.1.0]hexane (for reference preparation procedure see WO2005/080382, 62.6 mg, 0.276 mmol) were dissolved in 1,2-Dichloroethane (DCE) (9 mL) and the mixture was stirred at room temperature for 20 minutes. Afterwards the solution was cooled down to 0° C. and NaBH(AcO)$_3$ (80 mg, 0.376 mmol) was added. The mixture was stirred at rt overnight. The day after it was quenched with water and diluted with DCM. The mixture was filtered and extracted; organic phase was washed with water and NaHCO3 saturated solution and solvent was eliminated under reduced pressure. Crude product was purified by flash chromatography (DCM to DCM/MeOH/NH3 9:1:0.1) affording the title compound 6-methyl-4-(phenylcarbonyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (102 mg, 0.143 mmol, 57.1% yield). 6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione formed during the reaction was recovered (25 mg, 0.063 mmol).

MS (ES) (m/z): 499.21 [M+H]$^+$.

Preparation 5:
6-bromo-1,2,4-triazine-3,5(2H,4H)-dione (P5)

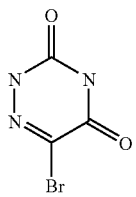

Bromine (2.506 mL, 48.6 mmol) was added to a suspension of 1,2,4-triazine-3,5(2H,4H)-dione (commercially available from Aldrich, 2.5 g, 22.11 mmol) in Water (40 mL). The mixture was stirred at room temperature for 26 hours. A white precipitate was formed. The solid was recovered by filtration and recrystallized from water (15 mL at reflux temperature) affording the title compound 6-bromo-1,2,4-triazine-3,5(2H,4H)-dione (1.97 g, 10.26 mmol, 46.4% yield) as a white crystalline solid.

MS (ES) (m/z): 191.95 [M]$^+$.

Preparation 6: 2-acetyl-6-bromo-1,2,4-triazine-3,5(2H,4H)-dione (P6)

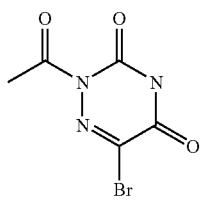

6-bromo-1,2,4-triazine-3,5(2H,4H)-dione (P5, 2.1 g, 10.94 mmol) was suspended in acetic anhydride (6.19 ml, 65.6 mmol) and the reaction mixture was refluxed for 2 hours.

Mixture was then cooled down to room temperature and evaporated under reduced pressure. The residue was repeatedly treated with toluene to afford 2-acetyl-6-bromo-1,2,4-triazine-3,5(2H,4H)-dione (2.47 g, 10.56 mmol, 96% yield) as a light pink solid. This was used for next step without purification.

MS (ES) (m/z): 233.95 [M]$^+$.

Preparation 7: 3-[6-bromo-3,5-dioxo-4-(phenylcarbonyl)-4,5-dihydro-1,2,4-triazin-2(3H)-yl]propanal (P7)

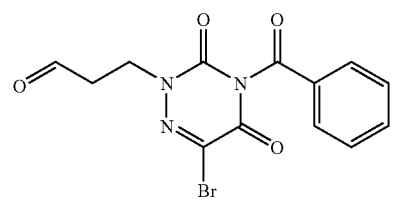

Step a:
2-acetyl-6-bromo-1,2,4-triazine-3,5(2H,4H)-dione (P6, 2.47 g, 10.56 mmol) was dissolved in 1,4-Dioxane (18 ml) and pyridine (2.56 ml, 31.7 mmol). The solution was cooled to 5° C. then benzoyl chloride (1.470 ml, 12.67 mmol) was added dropwise and the mixture was stirred at room temperature overnight. The day after the reaction mixture was diluted with AcOEt and washed with 0.5N HCl aq solution. Organic phase was separated, dried over Na$_2$SO$_4$, filtered and concentrated under reduced pressure. Crude product (brown oil) was purified by flash chromatography (SiO$_2$, eluent: Cy to Cy/AcOEt 6:4) affording 6-bromo-4-(phenylcarbonyl)-1,2,4-triazine-3,5(2H,4H)-dione (1.46 g, 4.93 mmol, 46.7% yield) as a white powder.

Step b:
To a stirring solution of 6-bromo-4-(phenylcarbonyl)-1,2,4-triazine-3,5(2H,4H)-dione (1.46 g, 4.93 mmol) in dry N,N-Dimethylformamide (DMF) (64.9 ml), TRIETHYLAMINE (0.825 ml, 5.92 mmol) was added and the mixture was stirred at room temperature for 15 minutes. Acrolein (0.366 ml, 4.93 mmol) was then added and the mixture was left stirring at room temperature for 3 hours. It was then quenched with NH$_4$Cl saturated solution and diluted with AcOEt. Phases were separated, organic phase was washed with cold water, dried over sodium sulphate, filtered and concentrated under reduced pressure affording 3-[6-bromo-3,5-dioxo-4-(phenylcarbonyl)-4,5-dihydro-1,2,4-triazin-2(3H)-yl]propanal (1.8 g, 5.11 mmol). The compound was used for next step without purification.

1H NMR (400 MHz, CHLOROFORM-d): δ ppm 9.86 (s, 1H), 7.97-7.92 (m, 2H), 7.61-7.53 (m, 3H), 4.40-4.34 (t, 2H), 3.08-3.02 (t, 2H).

Preparation 8: 6-bromo-2-(3-{(1S,5R)-1-[4-(trifluoromethyl)phenyl]-3-azabicyclo[3.1.0]hex-3-yl}propyl)-1,2,4-triazine-3,5(2H,4H)-dione (P8)

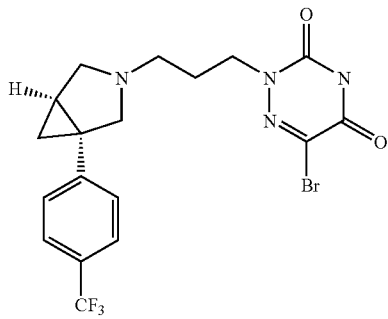

3-[6-bromo-3,5-dioxo-4-(phenylcarbonyl)-4,5-dihydro-1,2,4-triazin-2(3H)-yl]propanal (P8, 1.6 g, 4.54 mmol) was dissolved in dry 1,2-Dichloroethane (DCE) (10.200 mL), then (1S,5R)-1-[4-(trifluoromethyl)phenyl]-3-azabicyclo[3.1.0]hexane (prepared as described in WO2005/080382, 1.136 g, 5.00 mmol) was added and the mixture was stirred at room temperature for 10 minutes. The mixture was then cooled to 0° C. and left stirring for 15 minutes. Afterwards, sodiumtriacethoxy borohydride (1.059 g, 5.00 mmol) was added and the mixture was stirred at 0° C. for 2 hours. In situ cleavage of the N-benzoyl protecting group was observed. The mixture was then quenched with NH₄Cl saturated solution and extracted with DCM. Organic phase was dried and concentrated under reduced pressure affording a crude as a yellow oil. The latter was purified by flash chromatography (eluent: DCM to DCM/MeOH 95:5) affording 6-bromo-2-(3-{(1S,5R)-1-[4-(trifluoromethyl)phenyl]-3-azabicyclo[3.1.0]hex-3-yl}propyl)-1,2,4-triazine-3,5(2H,4H)-dione (362 mg, 0.788 mmol, 17.35% yield) as a white powder.

MS (ES) (m/z): 458.95 [M]⁺.

Preparation 9: 1-{[2,4-bis(methyloxy)phenyl]methyl}-3-bromo-4-methyl-1H-pyrrole-2,5-dione (P9)

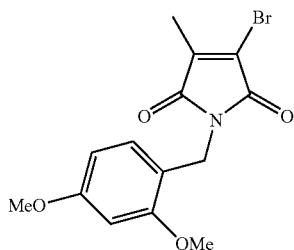

3-bromo-4-methyl-2,5-furandione (prepared as described in Org. and Bimolecular chemistry, pag 1782, 2004; 4.8 g, 25.1 mmol) and {[2,4-bis(methyloxy)phenyl]methyl}amine (3.78 mL, 25.1 mmol) were dissolved in acetic acid (100 mL) and the mixture was stirred at 100° C. overnight. Solvent was then concentrated under reduced pressure, additional acetic acid (100 mL) was added followed by sodium acetate (1.443 g, 17.59 mmol) and the mixture was refluxed for further 3 hours. Solvent was eliminated under reduced pressure and the residue was partitioned between DCM and water. Organic phase was washed with water, dried and solvent was eliminated under reduced pressure providing a crude that was purified by flash chromatography (eluent: Cy to Cy/AcOEt 7:3) affording 1-{[2,4-bis(methyloxy)phenyl]methyl}-3-bromo-4-methyl-1H-pyrrole-2,5-dione (8.55 g, 25.1 mmol, 100% yield) as a light yellow solid.

MS (ES) (m/z): 342 [M]⁺.

Preparation 10: 1-{[2,4-bis(methyloxy)phenyl]methyl}-3-methyl-4-[4-(trifluoromethyl)phenyl]-1H-pyrrole-2,5-dione (P10)

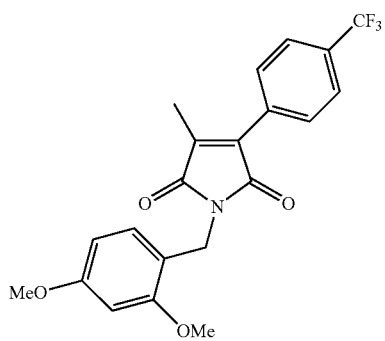

{[2,4-bis(methyloxy)phenyl]methyl}-3-bromo-4-methyl-1H-pyrrole-2,5-dione (P9, 3.3, 9.7 mmol), [4-(trifluoromethyl)phenyl]boronic acid (3.68 g, 19.40 mmol), bis(triphenylphosphine)palladium(ii) chloride (0.601 g, 0.91 mmol) and cesium fluoride (3.98 g, 26.2 mmol) and N,N-diethyl-N-(phenylmethyl)ethanaminium chloride (0.22 g, 0.970 mmol) were dissolved in Toluene (60 mL)/Water (60.0 mL) and the reaction mixture was stirred at 90° C. overnight. Toluene was evaporated under reduced pressure and a saturated solution of NH4Cl was added. The aqueous phase was extracted with DCM, solvent was eliminated under reduced pressure and crude product by flash chromatography (Biotage SiO2, eluent: Cy/AcOEt 98:2; fraction volume: 45 mL) affording 1-{[2,4-bis(methyloxy)phenyl]methyl}-3-methyl-4-[4-(trifluoromethyl)phenyl]-1H-pyrrole-2,5-dione (P10, 4.55 g, 11.22 mmol)

MS (ES) (m/z): 406.1 [M]⁺.

Preparation 11: 3-methyl-4-[4-(trifluoromethyl)phenyl]-1H-pyrrole-2,5-dione (P11)

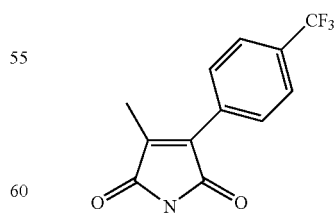

1-{[2,4-bis(methyloxy)phenyl]methyl}-3-methyl-4-[4-(trifluoromethyl)phenyl]-1H-pyrrole-2,5-dione (P10, 4.5 g 11.2 mmol), anisole (4.8 g, 44.4 mmol), trifluoracetic acid (38 mL) and concentrated sulphuric acid (0.58 mL) were heated at 90 C for 6 hours.

TFA was eliminated under reduced pressure and the residue was partitioned between DCM and a saturated solution of NaHCO3. Phases were separated and organic phase was dried, filtered and concentrated under reduced pressure. Crude was purified by flash chromatography (eluent: Cy to Cy/AcOEt 97:3) affording 3-methyl-4-[4-(trifluoromethyl)phenyl]-1H-pyrrole-2,5-dione (P11, 2.17 g, 8.50 mmol, 77% yield)

MS (ES) (m/z): 256 [M]+.

Preparation 12: (1R,5R/1S,5S)-1-methyl-5-[4-(trifluoromethyl)phenyl]-3-azabicyclo[3.1.0]hexane-2,4-dione (P12)

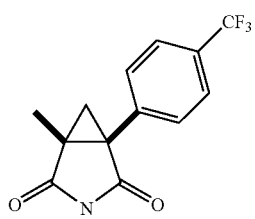

Trimethylsolfoxonium iodide (3.71 g, 16.85 mmol) and sodium hydride (0.674 g, 16.85 mmol) were dissolved in dry DMSO (45 mL) at 0° C. and the mixture was stirred at room temperature for 2 h. A solution of 3-methyl-4-[4-(trifluoromethyl)phenyl]-1H-pyrrole-2,5-dione (P11, 2.15 g, 8.43 mmol) in dry DMSO (45 mL) was then added and the reaction mixture was stirred at room temperature for 2 h.

Reaction was quenched with NH4Cl saturated solution and extracted with Et2O. Organic phase was washed with cold water and brine, dried over sodium solfate and solvent eliminated under reduced pressure. Crude product was purified by flash chromatography (eluent: Cy to Cy/AcOEt 6:4) affording 1-methyl-5-[4-(trifluoromethyl)phenyl]-3-azabicyclo[3.1.0]hexane-2,4-dione (P12, 1.48 g, 5.50 mmol, 65.3% yield) as a white solid.

MS (ES) (m/z): 269 [M]+.

Preparation 13: (1R,5R/1S,5S)-1-methyl-5-[4-(trifluoromethyl)phenyl]-3-azabicyclo[3.1.0]hexane (P13)

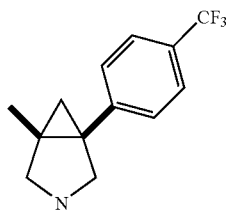

1-methyl-5-[4-(trifluoromethyl)phenyl]-3-azabicyclo[3.1.0]hexane-2,4-dione (P13, 1.48 g, 5.50 mmol) was dissolved in Tetrahydrofuran (THF) (39.3 ml), the mixture was cooled down to 0° C. and borane tetrahydrofurane complex (44.0 ml, 44.0 mmol) was slowly added. The reaction mixture was then refluxed for 7 h. The reaction mixture was cooled down to rt, MeOH (40 mL) and HCl 1N in Et2O (8 eq) were added slowly and the mixture was stirred at rt overnight. Solvents were removed under reduced pressure, additional MeOH (30 mL) and HCl 1N in Et2O (4 eq) were added and the mixture stirred at rt for 30 mins. Solvents were removed under reduced pressure and the residue was purified by a SCX. Ammonia fractions were collected and evaporated affording 1-methyl-5-[4-(trifluoromethyl)phenyl]-3-azabicyclo[3.1.0]hexane (P13, 960 mg, 3.98 mmol, 72.4% yield) as a white solid.

MS (ES) (m/z): 242 [M]+.

Preparation 14 and Preparation 15: (1S,5S or 1R,5R)-1-methyl-5-[4-(trifluoromethyl)phenyl]-3-azabicyclo[3.1.0]hexane (P14, Enantiomer 1) and (1R,5R or 1S,5S)-1-methyl-5-[4-(trifluoromethyl)phenyl]-3-azabicyclo[3.1.0]hexane (P15, Enantiomer 2)

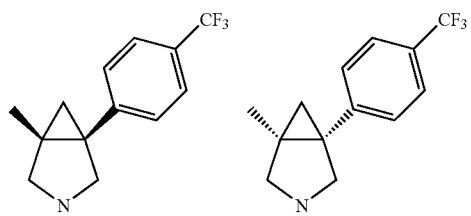

(1R,5R/1S,5S)-1-methyl-5-[4-(trifluoromethyl)phenyl]-3-azabicyclo[3.1.0]hexane (P13, 960 mg) was separated into the single enantiomers by preparative chiral HPLC, obtaining 418 mg of 1-methyl-5-[4-(trifluoromethyl)phenyl]-3-azabicyclo[3.1.0]hexane (P14, Enantiomer 1) and 424 mg of 1-methyl-5-[4-(trifluoromethyl)phenyl]-3-azabicyclo[3.1.0]hexane (P15, Enantiomer 2).

Preparative Chromatography:

| | |
|---|---|
| Column: | chiralpack AD-H |
| Mobile phase: | A: n-Hexane; B: Ethanol 80/20 v/v |
| Flow rate: | 14 mL/min |
| UV wavelengh range: | 220 nm |
| 70 mg/injection | |

| | | | |
|---|---|---|---|
| P14, Enantiomer 1: | ret. time (min) % a/a | 5.576 | 100% e.e. >99.5% |
| P15, Enantiomer 2: | ret. time (min) % a/a | 7.542 | 100% e.e. >99.5% |

Preparation 16: 6-bromo-(1R,5R or 1S,5S)2-(3-{1-methyl-5-[4-(trifluoromethyl)phenyl]-3-azabicyclo[3.1.0]hex-3-yl}propyl)-1,2,4-triazine-3,5(2H,4H)-dione (Enantiomer 2)(P16)

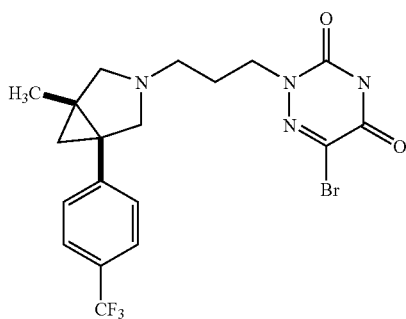

3-[6-bromo-3,5-dioxo-4-(phenylcarbonyl)-4,5-dihydro-1,2,4-triazin-2(3H)-yl]propanal (P7, 201 mg, 0.572 mmol) was dissolved in dry 1,2-Dichloroethane (DCE) (1.144 mL), then 1-methyl-5-[4-(trifluoromethyl)phenyl]-3-azabicyclo[3.1.0]hexane (P15, Enantiomer 2, 138 mg, 0.572 mmol) was added and the mixture was stirred at room temperature for 10 minutes. The mixture was then cooled to 0° C. and left stirring at that temperature for 15 minutes. Afterwards, sodiumtriacetoxy borohydride (133 mg, 0.629 mmol) was added and the mixture was stirred at 0° C. for 2 hours. In situ cleavage of the benzoyl nitrogen protecting group was observed. It was then quenched with NH$_4$Cl saturated solution and extracted with DCM. Organic phase was dried and concentrated under reduced pressure affording a crude as a yellow oil. The latter was purified by flash chromatography (SiO2, eluent: DCM to DCM/MeOH 95:5) affording 6-bromo-2-(3-{1-methyl-5-[4-(trifluoromethyl)phenyl]-3-azabicyclo[3.1.0]hex-3-yl}propyl)-1,2,4-triazine-3,5(2H,4H)-dione (Enantiomer 2, 48 mg, 0.101 mmol, 17.73% yield) as a white powder.

MS (ES) (m/z): 479.13 [M]$^+$.

Preparation 17:
2-Acetyl-1,2,4-triazine-3,5(2H,4H)-dione (P17)

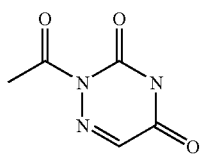

1,2,4-Triazine-3,5(2H,4H)-dione, commercially available from Alfa Aesar (800 mg, 7.07 mmol) was suspended in acetic anhydride (4 ml, 42.4 mmol) and the mixture was refluxed for 2 h. The reaction mixture was then cooled to room temperature and dried under vacuum. The crude product was repeatedly treated with toluene and concentrated under vacuum to give, as a light brown solid, the title compound (1.05 g, 96%) that was used in the next step without purification.

MS (ES) (m/z): 155.99 [M+H]$^+$ $^1$H NMR (400 MHz, DMSO-d$_6$) δ ppm 12.13-12.42 (m, 1H) 7.67-7.68 (m, 1H) 2.48-2.50 (m, 3H).

Preparation 18: 4-(Phenylcarbonyl)-1,2,4-triazine-3,5(2H,4H)-dione (P18)

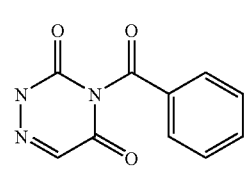

To a solution of 2-acetyl-1,2,4-triazine-3,5(2H,4H)-dione (1.05 g, 6.77 mmol) in 1,4-dioxane (11 ml) and pyridine (1.64 ml, 20.31 mmol) was treated dropwise at 5° C. with benzoyl chloride (0.90 ml, 7.78 mmol), then the mixture was stirred at room temperature overnight. The day after, 0.1 eq of benzoyl chloride was added and the mixture was stirred at rt for further 4 hours. The reaction mixture was then filtered to remove the piridinium salt and the filtered was evaporated under vacuum. The residue was dissolved in ethanol (23 ml) and then hydrochloride acid 37% (0.74 ml, 24.19 mmol) was added and the reaction was refluxed for 15 minutes. The solvent was evaporated under reduced pressure and the residue was purified by column chromatography on silica eluting with a gradient of methanol in DCM (from 0 to 4%) to afford the title compound as a white solid (0.35 g, 23.47%).

$^1$H NMR (400 MHz, DMSO-d6) δ ppm 12.94 (br. s., 1H) 8.12-8.16 (m, 2H) 7.80-7.85 (m, 1H) 7.71 (s, 1H) 7.59-7.65 (m, 2H)

Preparation 19: 2-acetyl-6-phenyl-1,2,4-triazine-3,5(2H,4H)-dione (P19)

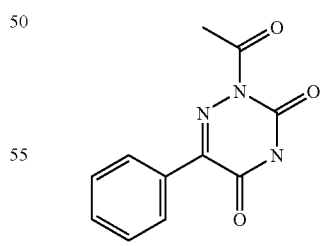

6-phenyl-1,2,4-triazine-3,5(2H,4H)-dione (prepared as described in BMCL, 2005, 43, 4363, 56 mg, 0.296 mmol) was heated in acetic anhydride (2 ml, 21.20 mmol) at 110° C. for 2 h, than was left at r.t. overnight. Solvent was evaporated under reduced pressure, obtaining 44 mg of title compound (64.3% yield).

MS (ES) (m/z): 190 [M-CH3CO]$^+$, 254 [M+Na]+

¹H-NMR (d-CDCl3) δ ppm 7.94-8.15 (m, 2H), 7.41-7.65 (m, 3H), 2.72 (s, 3H)

Preparation 20: 6-phenyl-4-(benzoyl)-1,2,4-triazine-3,5(2H,4H)-dione (P20)

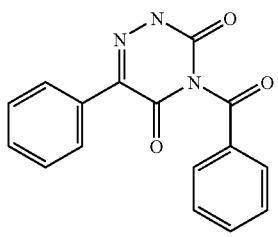

Benzoyl chloride (0.253 ml, 2.180 mmol) was added to a solution of 2-acetyl-6-phenyl-1,2,4-triazine-3,5(2H,4H)-dione (420 mg, 1.817 mmol) and pyridine (0.441 ml, 5.45 mmol) in 1,4-Dioxane (5 ml) at 5° C. Mixture was stirred at r.t. overnight. Solids were filtered off and rinsed with DCM, solvent was concentrated under reduced pressure. Residue was diluted in ethanol (20 ml), hydrochloric acid 37% in water (0.250 ml, 3.04 mmol) was added and mixture heated at 90° C. for 3 h. Solvent was concentrated and residue purified on biotage 25M silica cartridge, eluting with Cy/AcOEt 8:2 to AcOEt 100%, to give 87 mg of title compound (16% yield).

MS (ES) (m/z): 294 [M+H]⁺.

¹H-NMR (d-CDCl3) δ ppm 7.96-8.07 (m, 4H), 7.73 (d, 1H), 7.58 (t, 2H), 7.42-7.53 (m, 3H).

Preparation 21: 3-[3,5-dioxo-6-phenyl-4-(phenylcarbonyl)-4,5-dihydro-1,2,4-triazin-2(3H)-yl]propanal (P21)

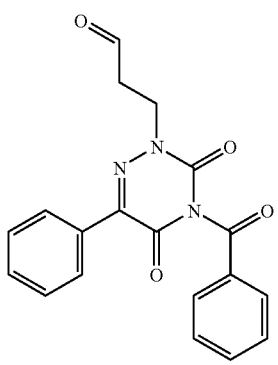

To a solution of 6-phenyl-4-(phenylcarbonyl)-1,2,4-triazine-3,5(2H,4H)-dione (84 mg, 0.286 mmol) in N,N-Dimethylformamide (DMF) (2 ml) under an argon atmosphere, triethylamine (0.050 ml, 0.359 mmol) was added and the mixture stirred at r.t. for 5 min., then acroleyn (0.020 ml, 0.299 mmol) was added and the mixture stirred overnight. Reaction was quenched by sat. NH4Cl (4 mL) and aq. layer extracted by Et2O (2×10 mL). Combined organic layers were washed by iced water, dried upon sodium sulphate and concentrated under reduced pressure to obtain 77 mg of title (77% yield).

MS (ES) (m/z): 350 [M+H]⁺.

¹H-NMR (d-CDCl3) δ ppm 9.89 (s, 1H), 7.95-8.02 (m, 2H), 7.67-7.75 (m, 1H), 7.55 (t, 2H), 7.41-7.50 (m, 3H), 4.46 (t, 2H), 3.05 (td, 2H).

Example 1

6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione (E1)

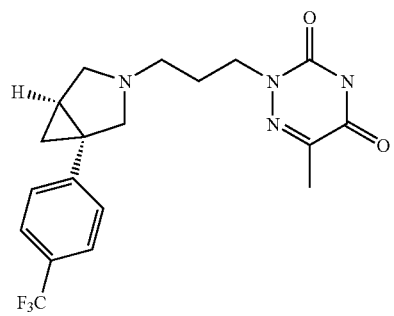

6-methyl-4-(phenylcarbonyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (P4, 102 mg, 0.205 mmol) was dissolved in a 2.0 M solution of ammonia in MeOH (2.046 ml, 4.09 mmol) and the mixture was stirred for 2 hours at rt. Solvent was eliminated under reduced pressure and crude was purified by flash chromatography (eluent DCM to DCM/MeOH/NH3 9:1:0.1) affording the title compound 6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione (E1, 67.7 mg, 0.172 mmol).

1H NMR (400 MHz, CHLOROFORM-d) δ: ppm 7.54 (d, 2H), 7.23 (d, 2H), 4.00 (t, 2H), 3.43 (d, 1H), 3.19 (d, 1H), 2.67-2.55 (m, 3H), 2.55-2.45 (m, 1H), 2.26 (s, 3H), 2.05-1.90 (m, 2H), 1.85-1.75 (m, 1H), 1.52-1.43 (m, 1H), 0.93-0.82 (m, 1H).

Example 2

6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione hydrochloride salt (E2)

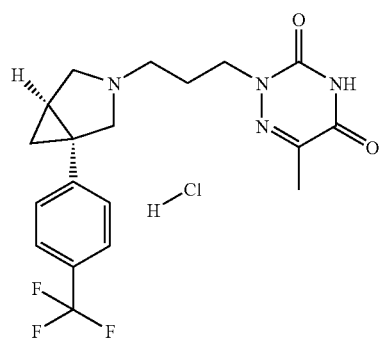

6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione was dissolved in Et2O and treated with HCl 1N in Et₂O to form the title compound 6-methyl-2-(3-{(1S,5R)-1-[4-(trifluoromethyl)phenyl]-3-azabicyclo[3.1.0]hex-3-yl}propyl)-1,2,4-triazine-3,5(2H,4H)-dione hydrochloride salt (E2, 73.8 mg, 0.171 mmol).

1H NMR (500 MHz, DMSO-d₆) δ: ppm 12.1 (s, 1H), 10.5 (s, 1H), 7.7 (2H, d), 7.4 (2H, d), 4.19 (2H, d), 3.8 (3H, m), 3.7 (2H, d), 3.5 (2H, d), 3.4 (2H, d), 3.2 (2H, m), 2.32 (1H, m), 2.21 (3H, s), 2.05-1.90 (m, 2H), 1.85-1.75 (m, 1H), 1.52-1.43 (m, 1H), 0.93-0.82 (m, 1H).

Example 3

6-(2-methyl-4-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E3)

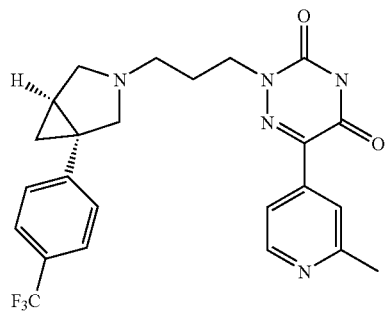

6-bromo-2-(3-{(1S,5R)-1-[4-(trifluoromethyl)phenyl]-3-azabicyclo[3.1.0]hex-3-yl}propyl)-1,2,4-triazine-3,5(2H,4H)-dione (P8,100 mg, 0.218 mmol) was suspended in a degassed mixture of 1,2-Dimethoxyethane (DME) (3.629 mL)/Water (0.726 mL), then 2-methyl-4-(4,4,5,5-tetramethyl-1,3,2-dioxaborolan-2-yl)pyridine (143 mg, 0.653 mmol), SODIUM CARBONATE (69.2 mg, 0.653 mmol), 2-biphenylyl(dicyclohexyl)phosphane (15.26 mg, 0.044 mmol) and Tetrakis (50.3 mg, 0.044 mmol) were added. The mixture was then heated at 90° C. and stirred at that temperature for 3 hours. The reaction mixture was then cooled down to room temperature, 2-methyl-4-(4,4,5,5-tetramethyl-1,3,2-dioxaborolan-2-yl)pyridine (143 mg, 0.653 mmol), 2-biphenylyl(dicyclohexyl)phosphane (15.26 mg, 0.044 mmol), SODIUM CARBONATE (69.2 mg, 0.653 mmol) and Tetrakis (50.3 mg, 0.044 mmol) were added again, the mixture was stirred at 90° C. for further 2 hours, then left stirring at room temperature overnight. The mixture was concentrated under reduced pressure and partitioned between AcOEt and water. Phases were separated, organic phase was dried over sodium sulphate and concentrated under reduced pressure. The residue was purified by Preparative HPLC affording 6-(2-methyl-4-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E3, 15.7 mg, 0.033 mmol, 15.29% yield).

1H NMR (400 MHz, CHLOROFORM-d) δ: ppm 8.65-8.58 (d, 1H), 7.86 (s, 1H), 7.8-7.75 (d, 1H), 7.57-7.51 (d, 2H), 7.25-7.19 (d, 2H), 4.24-4.14 (t, 2H), 3.48-3.40 (m, 1H), 3.24- 3.15 (m, 1H), 2.64-2.61 (m, 6H), 2.58-2.50 (m, 1H), 2.12-2.00 (m, 2H), 1.85-1.77 (m, 1H), 1.54-1.44 (m, 1H), 0.93-0.84 (m, 1H).

Example 4

6-(2-methyl-4-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E4)

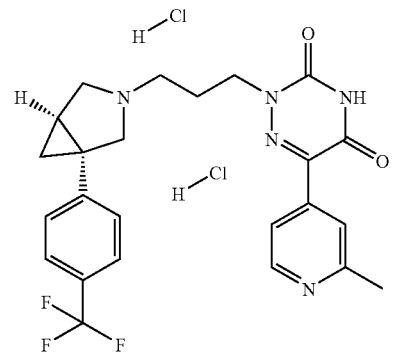

6-(2-methyl-4-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E3, 13 mg, 0.027 mmol) was dissolved in 2 mL of DCM and treated with HCl 1.25M in MeOH (2.2 eq) to form 6-(2-methyl-4-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E4, 14.8 mg, 0.027 mmol).

1H NMR (500 MHz, DMSO-d₆) δ: ppm 12.60 (s, 1H), 11.11-10.89 (br. s, 1H), 8.74-8.68 (m, 1H), 8.28-8.10 (m, 2H), 7.70-7.66 (d, 2H), 7.49-7.45 (d, 2H), 4.09-4.02 (m, 3H), 3.74-3.22 (m, 5H), 2.70 (s, 3H), 2.65-2.62 (m, 1H), 2.32-2.23 (m, 2H), 1.87-1.82 (m, 1H), 1.20-1.15 (m, 1H).

Example 5

6-(2-methyl-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E5)

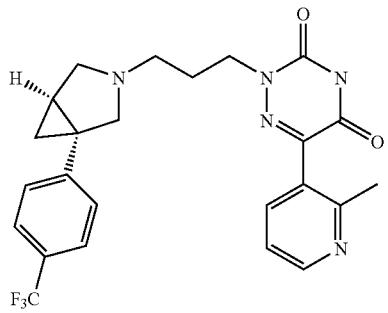

6-bromo-2-(3-{(1S,5R)-1-[4-(trifluoromethyl)phenyl]-3-azabicyclo[3.1.0]hex-3-yl}propyl)-1,2,4-triazine-3,5(2H,4H)-dione (P8, 100 mg, 0.218 mmol) was suspended in a degassed mixture of 1,2-Dimethoxyethane (DME) (3629 μl)/

Water (726 µl), then 2-methyl-3-(4,4,5,5-tetramethyl-1,3,2-dioxaborolan-2-yl)pyridine (167 mg, 0.653 mmol), SODIUM CARBONATE (92 mg, 0.871 mmol), 2-biphenylyl(dicyclohexyl)phosphane (15.26 mg, 0.044 mmol) and Tetrakis (50.3 mg, 0.044 mmol) were added. The mixture was then heated to 90° C. and stirred for 3 hours then it was cooled down to room temperature and 2-methyl-3-(4,4,5,5-tetramethyl-1,3,2-dioxaborolan-2-yl)pyridine (167 mg, 0.653 mmol), 2-biphenylyl(dicyclohexyl)phosphane (15.26 mg, 0.044 mmol), SODIUM CARBONATE (92 mg, 0.871 mmol) and Tetrakis (50.3 mg, 0.044 mmol) were added again. The mixture was stirred at 90° C. for further 1.5 hours until it was gone to completion.

Solvents were evaporated under reduced pressure and the residue was partitioned between AcOEt and water. Phases were separated and organic phase was dried over sodium sulphate, filtered and concentrated under reduced pressure. Crude was purified by Preparative HPLC, then further purified by flash chromatography (SiO2, DCM to DCM/MeOH 9:1) affording 6-(2-methyl-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E5, 41.5 mg, 0.088 mmol, 40.4% yield).

1H NMR (400 MHz, CHLOROFORM-d) δ: ppm 8.65-8.60 (m, 1H), 7.78-7.72 (m, 1H), 7.56-7.52 (m, 2H), 7.27-7.19 (m, 3H), 4.17-4.07 (m, 2H), 3.50-3.44 (m, 1H), 3.27-3.19 (m, 1H), 2.72-2.59 (m, 6H), 2.58-2.51 (m, 1H), 2.09-1.96 (m, 2H), 1.85-1.77 (m, 1H), 1.49-1.42 (m, 1H), 0.91-0.83 (m, 1H).

Example 6

6-(2-methyl-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E6)

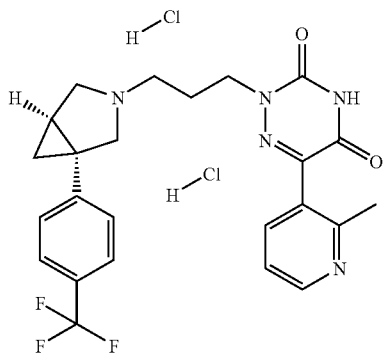

6-(2-methyl-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E5, 41.5 mg, 0.088 mmol) was dissolved in DCM and treated with 2.2 eq of HCl 1.25N in MeOH to form 6-(2-methyl-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E6, 43.1 mg, 0.079 mmol).

1H NMR (500 MHz, DMSO-d$_6$) δ: ppm 12.50-12.39 (m, 1H), 10.70 (br. s., 1H), 8.69-8.55 (m, 1H), 8.10-7.89 (m, 1H), 7.81-7.37 (m, 5H), 4.12-3.93 (m, 3H), 3.75-3.20 (m, 5H), 2.56 (s, 3H), 2.33-2.25 (m, 1H), 2.24-2.10 (m, 2H), 1.79-1.69 (m, 1H), 1.21-1.13 (m, 1H).

Example 7

6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E7)

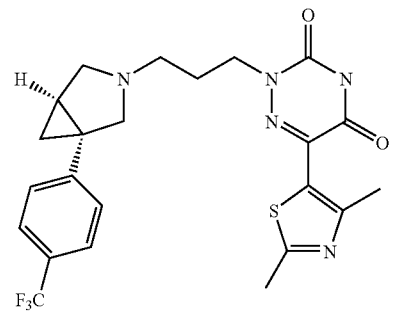

6-bromo-2-(3-{(1S,5R)-1-[4-(trifluoromethyl)phenyl]-3-azabicyclo[3.1.0]hex-3-yl}propyl)-1,2,4-triazine-3,5(2H,4H)-dione (P8, 170 mg, 0.370 mmol) was suspended in a degassed mixture of 1,2-Dimethoxyethane (DME) (6169 ply Water (1234 µl), then 2,4-dimethyl-5-(4,4,5,5-tetramethyl-1,3,2-dioxaborolan-2-yl)-1,3-thiazole (266 mg, 1.110 mmol), SODIUM CARBONATE (118 mg, 1.110 mmol), 2-biphenylyl(dicyclohexyl)phosphane (25.9 mg, 0.074 mmol) and Tetrakis (86 mg, 0.074 mmol) were added. The mixture was then heated at 90° C. and stirred at that temperature for 3 hours. Then the reaction mixture was cooled down to room temperature and 2,4-dimethyl-5-(4,4,5,5-tetramethyl-1,3,2-dioxaborolan-2-yl)-1,3-thiazole (266 mg, 1.110 mmol), 2-biphenylyl(dicyclohexyl)phosphane (25.9 mg, 0.074 mmol), SODIUM CARBONATE (118 mg, 1.110 mmol) and Tetrakis (86 mg, 0.074 mmol) were added again. The mixture was stirred at 90° C. for further 4 hours, then left stirring at room temperature overnight. The mixture was concentrated under reduced pressure and partitioned between AcOEt and water. Phases were separated, organic phase was dried over sodium sulphate and concentrated under reduced pressure. Crude product was purified by Preparative HPLC then further purified by flash chromatography (SiO2; eluent: DCM to DCM/MeOH 9:1) affording 6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E7, 44.3 mg, 0.090 mmol, 24.35% yield).

1H NMR (400 MHz, CHLOROFORM-d) δ: ppm 7.57-7.50 (d, 2H), 7.25-7.18 (d, 2H), 4.18-4.08 (m, 2H), 3.56-3.46

(m, 1H), 3.33-3.22 (m, 1H), 2.78-2.63 (m, 9H), 2.63-2.53 (m, 1H), 2.12-1.99 (m, 2H), 1.87-1.78 (m, 1H), 1.49-1.41 (m, 1H), 0.92-0.83 (m, 1H).

Example 8

6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E8)

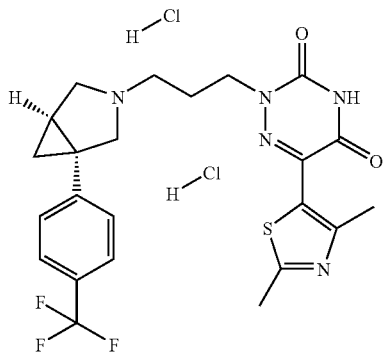

6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E7, 44.3 mg, 0.090 mmol) was dissolved in DCM and treated with HCl 1.25 M in MeOH (2.2 eq) affording after trituration with Et2O 6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E8, 41.4 mg, 0.073 mmol).

1H NMR (500 MHz, DMSO-$d_6$) δ: ppm 12.46 (s, 1H), 10.61 (br. S., 1H), 7.68 (d, 2H), 7.46 (d, 2H), 4.14-3.12 (m, 8H), 2.65-2.96 (m, 3H), 2.57-2.54 (m, 3H), 2.32-2.24 (m, 1H), 2.24-2.14 (m, 2H), 1.77-1.65 (m, 1H), 1.21-1.11 (m, 1H).

Example 9

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E9)

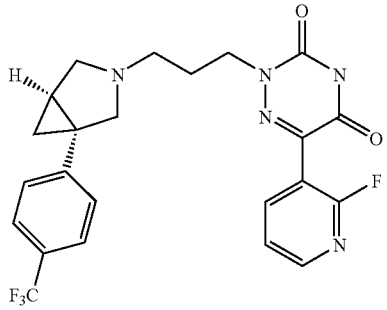

6-bromo-2-(3-{(1S,5R)-1-[4-(trifluoromethyl)phenyl]-3-azabicyclo[3.1.0]hex-3-yl}propyl)-1,2,4-triazine-3,5(2H,4H)-dione (P8, 100 mg, 0.218 mmol) was suspended in a degassed mixture of 1,2-Dimethoxyethane (DME) (3.629 ml)/Water (0.726 ml). Then (2-fluoro-3-pyridinyl)boronic acid (92 mg, 0.653 mmol), sodium carbonate (69.2 mg, 0.653 mmol), Tetrakis (50.3 mg, 0.044 mmol) and 2-biphenylyl (dicyclohexyl)phosphane (15.26 mg, 0.044 mmol) were added and the mixture was heated to 90° C. and stirred at that temperature for 3 hours. The mixture was cooled down to room temperature, diluted with 1.3 mL of a mixture of DME/Water (5:1) then 2-biphenylyl(dicyclohexyl)phosphane (15.26 mg, 0.044 mmol), (2-fluoro-3-pyridinyl)boronic acid (92 mg, 0.653 mmol), Tetrakis (50.3 mg, 0.044 mmol) and sodium carbonate (69.2 mg, 0.653 mmol) were added again. The reaction mixture was heated to 90° C. and left stirring at that temperature for 40 minutes. The reaction mixture was cooled down to room temperature and evaporated under reduced pressure. The residue was partitioned between AcOEt and water and extracted. Organic phase was dried over sodium sulphate, filtered and concentrated under reduced pressure. Crude product was purified by Preparative HPLC affording 6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E9, 47 mg, 0.099 mmol, 45.4% yield).

1H NMR (400 MHz, CHLOROFORM-d) δ: 8.36-8.28 (m, 1H), 8.16-8.05 (m, 1H), 7.57-7.49 (d, 2H), 7.35-7.29 (m, 1H), 7.26-7.19 (d, 2H), 4.17-4.07 (m, 2H), 3.61-3.52 (m, 1H), 3.36-3.26 (m, 1H), 2.81-2.66 (m, 3H), 2.65-2.56 (m, 1H), 2.11-1.99 (m, 2H), 1.87-1.78 (m, 1H), 1.50-1.42 (m, 1H), 0.94-0.84 (m, 1H).

Example 10

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E10)

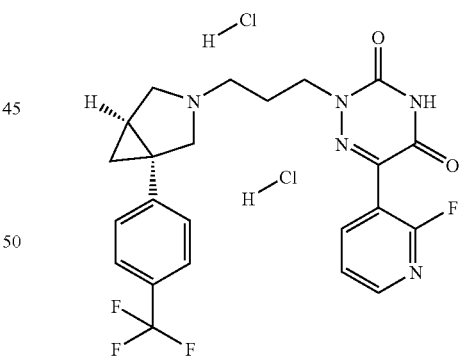

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (E9, 46 mg, was dissolved in 2 mL of DCM and treated with HCl 1.25M in MeOH (2.2 eq) to form 6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione dihydrochloride salt (E10, 45 mg, 0.082 mmol).

1H NMR (500 MHz, DMSO-$d_6$) δ: ppm 12.53-12.47 (m, 1H), 10.48-10.30 (m, 1H), 8.40-8.33 (m, 1H), 8.19-8.10 (m, 1H), 7.73-7.64 (m, 2H), 7.54-7.43 (m, 3H), 4.13-3.90 (m, 3H), 3.76-3.44 (m, 3H), 3.36-3.23 (m, 2H), 2.34-2.26 (m, 1H), 2.22-2.08 (m, 2H), 1.71-1.57 (m, 1H), 1.23-1.13 (m, 1H).

Example 11

6-(2-fluoro-3-pyridinyl)-2-(3-{(1S,5S or 1R,5S)-1-methyl-5-[4-(trifluoromethyl)phenyl]-3-azabicyclo[3.1.0]hex-3-yl}propyl)-1,2,4-triazine-3,5(2H,4H)-dione (Enantiomer 2) (E11)

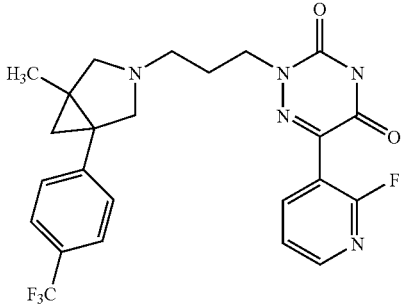

6-bromo-2-(3-{1-methyl-5-[4-(trifluoromethyl)phenyl]-3-azabicyclo[3.1.0]hex-3-yl}propyl)-1,2,4-triazine-3,5(2H,4H)-dione (P16, 48 mg, 0.101 mmol) was suspended in a degassed mixture of 1,2-Dimethoxyethane (DME) (1.725 mL)/Water (0.345 mL). Then (2-fluoro-3-pyridinyl)boronic acid (42.9 mg, 0.304 mmol), sodium carbonate (32.2 mg, 0.304 mmol), Tetrakis (23.44 mg, 0.020 mmol) and 2-biphenylyl(dicyclohexyl)phosphane (7.11 mg, 0.020 mmol) were added and the mixture was heated to 90° C. and stirred at that temperature for 3 hours. The mixture was cooled down to room temperature, diluted with 1.3 mL of a mixture of DME/Water (5:1) then 2-biphenylyl(dicyclohexyl)phosphane (7.11 mg, 0.020 mmol), (2-fluoro-3-pyridinyl)boronic acid (42.9 mg, 0.304 mmol), Tetrakis (23.44 mg, 0.020 mmol) and sodium carbonate (32.2 mg, 0.304 mmol) were added again. The reaction mixture was then heated to 90° C. and left stirring at that temperature for 40 minutes. The reaction mixture was cooled down to room temperature and evaporated under reduced pressure. The residue was partitioned between AcOEt and water and extracted. Organic phase was dried over sodium sulphate, filtered and concentrated under reduced pressure. Crude product was purified by Preparative HPLC then further purified by flash chromatography (SiO2, DCM to DCM/MeOH 9:1) affording 6-(2-fluoro-3-pyridinyl)-2-(3-{1-methyl-5-[4-(trifluoromethyl)phenyl]-3-azabicyclo[3.1.0]hex-3-yl}propyl)-1,2,4-triazine-3,5(2H,4H)-dione (Enantiomer 2) (E11, 14 mg, 0.029 mmol, 28.2% yield).

1H NMR (400 MHz, CHLOROFORM-d) δ: 8.36-8.29 (m, 1H), 8.14-8.06 (m, 1H), 7.61-7.54 (d, 2H), 7.42-7.34 (d, 2H), 7.33-7.29 (m, 1H), 4.16-4.07 (m, 2H), 3.45-3.37 (m, 1H), 3.37-3.29 (m, 1H), 2.78-2.64 (m, 3H), 2.50-2.42 (m, 1H), 2.09-1.95 (m, 2H), 1.46-1.40 (m, 1H), 0.97 (s, 3H), 0.83-0.74 (m, 1H).

Example 12

6-(2-fluoro-3-pyridinyl)-2-(3-{(1S,5S or 1R,5S)-{1-methyl-5-[4-(trifluoromethyl)phenyl]-3-azabicyclo[3.1.0]hex-3-yl}propyl)-1,2,4-triazine-3,5(2H,4H)-dione dihydrochloride salt (Enantiomer 2) (E12)

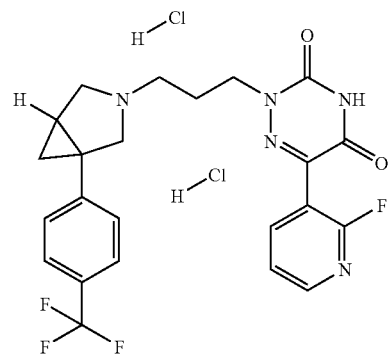

6-(2-fluoro-3-pyridinyl)-2-(3-{1-methyl-5-[4-(trifluoromethyl)phenyl]-3-azabicyclo[3.1.0]hex-3-yl}propyl)-1,2,4-triazine-3,5(2H,4H)-dione (E11, 14 mg, 0.029 mmol) was dissolved in 2 mL of DCM and treated with HCl 1.25M in MeOH (2.2 eq) to form 6-(2-fluoro-3-pyridinyl)-2-(3-{1-methyl-5-[4-(trifluoromethyl)phenyl]-3-azabicyclo[3.1.0]hex-3-yl}propyl)-1,2,4-triazine-3,5(2H,4H)-dione dihydrochloride salt (Enantiomer 2) (E12, 15.7 mg, 0.028 mmol).

1H NMR (500 MHz, DMSO-d$_6$) δ: ppm 12.60-12.42 (m, 1H), 10.13 (br. s., 1H), 8.41-8.31 (m, 1H), 8.22-8.05 (m, 1H), 7.84-7.62 (m, 4H), 7.55-7.42 (m, 1H), 4.08-3.95 (m, 2H), 3.91-3.58 (m, 3H), 3.48-3.29 (m, 3H), 2.22-2.00 (m, 2H), 1.65-1.55 (m, 1H), 1.27-1.17 (m, 1H), 0.91 (s, 3H).

Example 13

2-(3-{(1S,5R)-1-[4-(trifluoromethyl)phenyl]-3-azabicyclo[3.1.0]hex-3-yl}propyl)-1,2,4-triazine-3,5(2H,4H)-dione (E13)

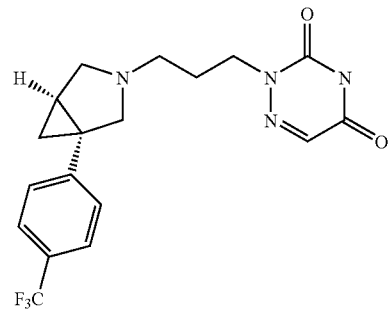

To a stirred solution of 4-(phenylcarbonyl)-1,2,4-triazine-3,5(2H,4H)-dione (100 mg, 0.46 mmol) in N,N-Dimethylformamide (DMF) (2 ml), triethylamine (0.077 ml, 0.55 mmol) was added and the mixture was stirred for 5 min at room temperature. Then 2-propenal 90% (0.034 ml, 0.46 mmol) was added and the reaction was stirred for 18 hours at room temperature.

The reaction was quenched with an aq. sat solution of NH$_4$Cl and the organic layers were extracted with ethyl acetate (EA). The organic layers were combined, dried over anhydrous Na$_2$SO$_4$, filtered and concentrated in vacuo affording 3-[3,5-dioxo-4-(phenylcarbonyl)-4,5-dihydro-1,2,4-triazin-2(3H)-yl]propanal as a crude product that was used for next step without purification.

The crude obtained was dissolved in 1,2-dichloroethane (DCE) (4 ml), (1S,5R)-1-[4-(trifluoromethyl)phenyl]-3-azabicyclo[3.1.0]hexane (94 mg, 0.41 mmol) and acetic acid (0.079 ml, 1.38 mmol) were added at 0° C. After 15 minutes, sodium triacetoxyborohydride (107 mg, 0.51 mmol) was added and the mixture was stirred at 0° C. for 4 hours. The reaction was quenched with sat. aq. solution of NaHCO$_3$ and the organic layers were extracted with dichloromethane (DCM). The organic layers were combined, dried over Na$_2$SO$_4$, filtered and concentrated in vacuo. The crude compound obtained was passed through a SCX (2 g) cartridge eluiting firstly with methanol and then eluiting with solution NH$_3$ in MeOH 1M. Ammonia fractions were collected and the solvent was evaporated.

The crude obtained was then dissolved in ammonia (5 ml) 2M solution in MeOH and stirred at room temperature for 1 hour. The reaction mixture was concentrated in vacuo and the crude was purified by column chromatography on silica (12M) eluting with a gradient of methanol in DCM (from 0% to 5%) affording 2-(3-{(1S,5R)-1-[4-(trifluoromethyl)phenyl]-3-azabicyclo[3.1.0]hex-3-yl}propyl)-1,2,4-triazine-3,5(2H,4H)-dione (40 mg, 0.105 mmol, 22.8%) as a colorless oil.

MS (ES) (m/z): 381.1 [M+H]$^+$

1H NMR (400 MHz, CHLOROFORM-d) δ ppm 7.53 (d, 2H) 7.38 (s, 1H) 7.20 (d, 2H) 4.03 (t, 2H) 3.38 (d, 1H) 3.14 (d, 1H) 2.54-2.64 (m, 3H) 2.47 (dd, 1H) 1.89-1.98 (m, 2H) 1.73-1.79 (m, 1H) 1.45 (t, 1H) 0.84 (dd, 1H)

Example 14

6-phenyl-2-(3-{(1S,5R)-1-[4-(trifluoromethyl)phenyl]-3-azabicyclo[3.1.0]hex-3-yl}propyl)-1,2,4-triazine-3,5(2H,4H)-dione (E14)

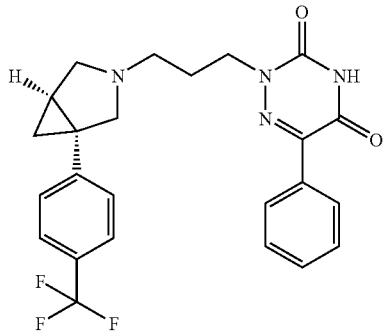

To a stirred solution of (1S,5R)-1-[4-(trifluoromethyl)phenyl]-3-azabicyclo[3.1.0]hexane (115 mg, 0.506 mmol), 3-[3,5-dioxo-6-phenyl-2-(phenylcarbonyl)-2,5-dihydro-1,2,4-triazin-4(3H)-yl]propanal (77 mg, 0.220 mmol) and acetic acid (0.04 ml, 0.699 mmol), sodium triacetoxyborohydride (56.1 mg, 0.264 mmol) was added portionwise at 0° C. under an argon atmosphere. Mixture was stirred at 0° C. for 4 h.

Reaction was quenched with NaHCO3 sat. sol. (5 mL) and aq. layer extracted by DCM (2×10 mL). Combined organic layers were washed by brine (5 mL) dried upon sodium sulphate and concentrated under reduced pressure.

Residue was purified on 5 g SCX cartridge eluting with MeOH followed by of 2M methanolic ammonia. Ammonia phase was concentrated, residue was desolved in dichloromethane (4 ml), and PS-isocyanate (220 mg, 0.331 mmol) was added, mixture was shaken at r.t. for 4 h to scavenge the resudual [3.1.0] amine.

Solvent was evaporated and the crude purified on 3 g SCX cartridge, eluting with MeOH followed by 2M methanolic ammonia. Product was furtherly purified by fraction lynx (generic basic method), obtaining 9 mg of title compound. (8.5% yield).

MS (ES) (m/z): 457 [M+H]$^+$.

$^1$H-NMR (d-CDCl3) δ: 8.45 (br. s., 1H), 8.02 (m, 2H), 7.53 (d, 2H), 7.46 (m, 3H), 7.21 (d, 2H), 4.14 (t, 2H), 3.38 (d, 1H), 3.14 (d, 1H), 2.63 (m, 3H), 2.48 (dd, 1H), 2.02 (m, 2H), 1.77 (m, 1H), 1.49 (t, 1H), 0.85 (dd, 1H).

Example 15

6-phenyl-2-(3-{(1S,5R)-1-[4-(trifluoromethyl)phenyl]-3-azabicyclo[3.1.0]hex-3-yl}propyl)-1,2,4-triazine-3,5(2H,4H)-dione hydrochloride (E15)

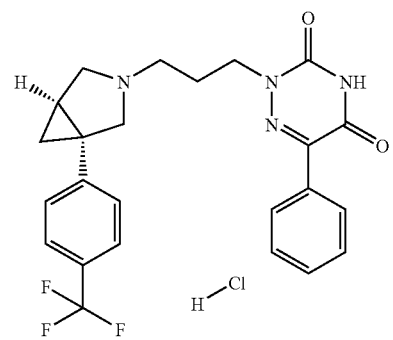

6-phenyl-2-(3-{(1S)-1-[4-(trifluoromethyl)phenyl]-3-azabicyclo[3.1.0]hex-3-yl}propyl)-1,2,4-triazine-3,5(2H,4H)-dione (9 mg 0.019 mmol) was diluted in diethyl ether (1 ml) and hydrochloric acid 1M in Et2O (0.022 ml, 0.022 mmol) under nitrogen atmosphere. Solvent was removed and the residue triturated in Et2O (2×1 mL), obtaining 3.2 mg of title compound as a white solid (27% yield).

MS (ES) (m/z): 457 [M+H]$^+$.

$^1$H-NMR (MeOD) δ ppm 7.95-8.07 (m, 2H), 7.61-7.72 (m, 2H), 7.38-7.55 (m, 5H), 4.12-4.27 (m, 3H), 3.84-3.94 (m, 1H), 3.59-3.78 (m, 2H), 3.39-3.50 (m, 2H), 2.22-2.41 (m, 3H), 1.39-1.47 (m, 1H), 1.32-1.39 (m, 1H).

$^1$H-NMR (d-CDCl3) δ: 8.45 (br. s., 1H), 8.02 (m, 2H), 7.53 (d, 2H), 7.46 (m, 3H), 7.21 (d, 2H), 4.14 (t, 2H), 3.38 (d, 1H), 3.14 (d, 1H), 2.63 (m, 3H), 2.48 (dd, 1H), 2.02 (m, 2H), 1.77 (m, 1H), 1.49 (t, 1H), 0.85 (dd, 1H).

Example 16

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione hydrochloride (E16)

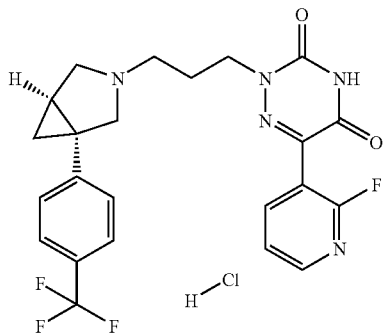

6-(2-fluoro-3-pyridinyl)-2-(3-{(1S,5R)-1-[4-(trifluoromethyl)phenyl]-3-azabicyclo[3.1.0]hex-3-yl}propyl)-1,2,4-triazine-3,5(2H,4H)-dione (19.7 mg 0.041 mmol, prepared following an analoguos procedure to that described for Ex9) was diluted in diethyl ether (1 ml) and hydrochloric acid 1M in Et2O (0.045 ml, 0.045 mmol) under nitrogen atmosphere. Solvent was removed and the residue triturated in Et2O (2×1 mL), obtaining 21.8 mg of title compound as a white solid.
1H NMR (500 MHz, DMSO-$d_6$) δ: ppm 12.53-12.47 (m, 1H), 10.48-10.30 (m, 1H), 8.40-8.33 (m, 1H), 8.19-8.10 (m, 1H), 7.73-7.64 (m, 2H), 7.54-7.43 (m, 3H), 4.13-3.90 (m, 3H), 3.76-3.44 (m, 3H), 3.36-3.23 (m, 2H), 2.34-2.26 (m, 1H), 2.22-2.08 (m, 2H), 1.71-1.57 (m, 1H), 1.23-1.13 (m, 1H).

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of formula (IB)', or a salt thereof:

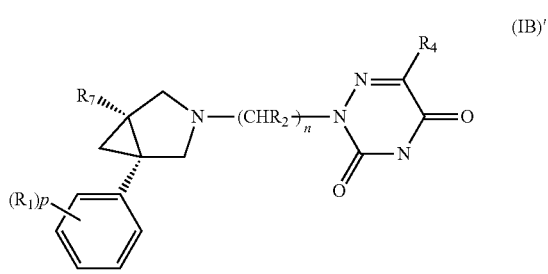

wherein
p is an integer ranging from 0 to 5;
$R_1$ is halogen, hydroxy, cyano, $C_{1-4}$alkyl, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 3, 4, 5 or 6;
$R_6$ is a moiety selected from the group consisting of isoxazolyl, —CH₂—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from the group consisting of halogen, cyano, $C_{1-4}$alkyl, $C_{1-4}$alkoxy, and $C_{1-4}$alkanoyl;
$R_4$ is selected from the group consisting of hydrogen, halogen, hydroxy, cyano, $C_{1-4}$alkyl, $C_{3-7}$ cycloalkyl, halo$C_{1-4}$ alkyl, halo$C_{1-4}$alkoxy, $C_{1-4}$alkanoyl and NR'R"; or $R_4$ is a phenyl group, a 5-14 membered heterocyclic group; and any of such phenyl or heterocyclic group is optionally substituted by 1, 2, 3 or 4 substituents selected from the group consisting of halogen, cyano, $C_{1-4}$alkoxy, $C_{1-4}$alkanoyl, halo$C_{1-4}$alkoxy and $SF_5$;
$R_7$ is hydrogen or $C_{1-2}$alkyl;
R' is H, $C_{1-4}$ alkyl or $C_{1-4}$ alkanoyl;
R" is H, $C_{1-4}$ alkyl or $C_{1-4}$alkanoyl; or
R' and R" taken together with the interconnecting nitrogen atom may form a 5-, 6-membered saturated or an unsaturated heterocyclic ring.

2. A compound of formula (IB)' according to claim 1, which is:
6-methyl-2-(3-{(1S,5R)-1-[4-(trifluoromethyl)phenyl]-3-azabicyclo[3.1.0]hex-3-yl}propyl)-1,2,4-triazine-3,5 (2H,4H)-dione;
6-(2-methyl-4-pyridinyl)-2-(3-{(1S,5R)-1-[4-(trifluoromethyl)phenyl]-3-azabicyclo[3.1.0]hex-3-yl}propyl)-1, 2,4-triazine-3,5(2H,4H)-dione;
6-(2-methyl-3-pyridinyl)-2-(3-{(1S,5R)-1-[4-(trifluoromethyl)phenyl]-3-azabicyclo[3.1.0]hex-3-yl}propyl)-1, 2,4-triazine-3,5(2H,4H)-dione;
6-(2,4-dimethyl-1,3-thiazol-5-yl)-2-(3-{(1S,5R)-1-[4-(trifluoromethyl)phenyl]-3-azabicyclo[3.1.0]hex-3-yl}propyl)-1,2,4-triazine-3,5(2H,4H)-dione;
6-(2-fluoro-3-pyridinyl)-2-(3-{(1S,5R)-1-[4-(trifluoromethyl)phenyl]-3-azabicyclo[3.1.0]hex-3-yl}propyl)-1, 2,4-triazine-3,5(2H,4H)-dione;
6-(2-fluoro-3-pyridinyl)-2-(3-{1-methyl-5-[4-(trifluoromethyl)phenyl]-3-azabicyclo[3.1.0]hex-3-yl}propyl)-1,2,4-triazine-3,5(2H,4H)-dione (Enantiomer 2);
2-(3-{(1S,5R)-1-[4-(trifluoromethyl)phenyl]-3-azabicyclo[3.1.0]hex-3-yl}propyl)-1,2,4-triazine-3,5(2H,4H)-dione;
6-phenyl-2-(3-{(1S,5R)-1-[4-(trifluoromethyl)phenyl]-3-azabicyclo[3.1.0]hex-3-yl}propyl)-1,2,4-triazine-3,5 (2H,4H)-dione;
6-(2-fluoro-3-pyridinyl)-2-(3-{(1S,5R)-1-[4-(trifluoromethyl)phenyl]-3-azabicyclo[3.1.0]hex-3-yl}propyl)-1, 2,4-triazine-3,5(2H,4H)-dione;
or a salt thereof.

3. A method of treating a condition for which modulation of dopamine $D_3$ receptors is beneficial, which comprises administering to a mammal in need thereof an effective amount of a compound as claimed in claim 1, wherein the condition is psychosis or a psychotic condition, substance abuse, or premature ejaculation.

4. A pharmaceutical composition comprising a compound as claimed in claim 1, or a pharmaceutically acceptable salt thereof, in association with a pharmaceutically acceptable carrier.

* * * * *